United States Patent
Kojima

(10) Patent No.: US 10,780,458 B2
(45) Date of Patent: Sep. 22, 2020

(54) ULTRASOUND SENSOR AND METHOD OF MANUFACTURING THEREOF

(71) Applicant: SEIKO EPSON CORPORATION, Tokyo (JP)

(72) Inventor: Chikara Kojima, Matsumoto (JP)

(73) Assignee: Seiko Epson Corporation (JP)

(*) Notice: Subject to any disclaimer, the term of this patent is extended or adjusted under 35 U.S.C. 154(b) by 568 days.

(21) Appl. No.: 15/324,140

(22) PCT Filed: Jul. 9, 2015

(86) PCT No.: PCT/JP2015/069810
§ 371 (c)(1),
(2) Date: Jan. 5, 2017

(87) PCT Pub. No.: WO2016/006671
PCT Pub. Date: Jan. 14, 2016

(65) Prior Publication Data
US 2017/0157647 A1 Jun. 8, 2017

(30) Foreign Application Priority Data
Jul. 9, 2014 (JP) .................................. 2014-141778

(51) Int. Cl.
*B06B 1/06* (2006.01)
*G01S 15/89* (2006.01)
(Continued)

(52) U.S. Cl.
CPC .......... *B06B 1/0622* (2013.01); *A61B 8/4427* (2013.01); *B06B 1/0629* (2013.01);
(Continued)

(58) Field of Classification Search
CPC ....... B06B 1/06; B06B 1/0603; B06B 1/0622; B06B 1/0629; H01L 41/047
(Continued)

(56) References Cited

U.S. PATENT DOCUMENTS

| 2008/0013405 A1 | 1/2008 | Moon et al. |
| 2012/0176002 A1* | 7/2012 | Kim .......................... H04R 3/04 310/317 |

(Continued)

FOREIGN PATENT DOCUMENTS

| JP | 2004159811 A | 6/2004 |
| JP | 2006075425 A | 3/2006 |

(Continued)

OTHER PUBLICATIONS

Extended European Search Report for Application No. EP 15 81 8492 dated Apr. 17, 2018 (9 pages).

*Primary Examiner* — Derek J Rosenau
(74) *Attorney, Agent, or Firm* — Harness, Dickey & Pierce, P.L.C.

(57) ABSTRACT

An ultrasound sensor includes: a diaphragm; a plurality of first electrodes; a plurality of second electrodes; and a plurality of piezoelectric layers which is provided between the first electrode and the second electrode, in which, in a Z-direction, a portion in which the first electrode, the piezoelectric layer and the second electrode are overlapped is referred to as an active portion, and a range to the extent that the diaphragm is oscillatable by driving the active portion is referred to as a movable portion, when a unit including one movable portion and the active portion which is provided within the one movable portion is referred to as one ultrasound element in plan view, two or more types of ultrasound elements in which a dimension of the active portion with respect to a dimension of the movable portion is different from each other in plan view are provided.

6 Claims, 22 Drawing Sheets

(51) Int. Cl.
*A61B 8/00* (2006.01)
*H01L 41/29* (2013.01)
*H01L 41/31* (2013.01)

(52) U.S. Cl.
CPC .......... *G01S 15/8925* (2013.01); *H01L 41/29* (2013.01); *H01L 41/31* (2013.01); *A61B 8/4444* (2013.01); *A61B 8/4488* (2013.01)

(58) Field of Classification Search
USPC .................. 310/322, 334, 335, 365, 366
See application file for complete search history.

(56) References Cited

U.S. PATENT DOCUMENTS

| | | |
|---|---|---|
| 2013/0324853 A1 | 12/2013 | Matsuda |
| 2014/0066778 A1 | 3/2014 | Nishiwaki |
| 2015/0258573 A1* | 9/2015 | Kojima ................ G10K 11/002 310/327 |

FOREIGN PATENT DOCUMENTS

| | | |
|---|---|---|
| JP | 2008020429 A | 1/2008 |
| JP | 2010-164331 A | 7/2010 |
| JP | 2010-165028 A | 7/2010 |
| JP | 2013055978 A | 3/2013 |
| JP | 2013243513 A | 12/2013 |

\* cited by examiner

A-A'

B-B'

C-C'

D-D' b-b' c-c' b-b' c-c' b-b' c-c' b-b' c-c' b-b' c-c' b-b' c-c' b-b' c-c' b-b' c-c' b-b' c-c'

E-E'

ULTRASOUND SENSOR AND METHOD OF MANUFACTURING THEREOF

CROSS-REFERENCE TO RELATED APPLICATIONS

This application is a U.S. National Phase Application under 35 U.S.C. 371 of International Application No. PCT/JP2015/069810, filed on Jul. 9, 2015 and published in Japanese as WO 2016/006671 on Jan. 14, 2016. This application claims priority to Japanese Patent Application No. 2014-141778, filed on Jul. 9, 2014. The entire disclosures of the above applications are incorporated herein by reference.

TECHNICAL FIELD

The present invention relates to an ultrasound sensor and a method of manufacturing thereof.

BACKGROUND ART

Ultrasound sensors in which a semiconductor substrate having an opening portion, two layers of electrodes on an insulating film layer formed on the surface of the semiconductor substrate while blocking the opening portion and a PZT ceramic thin film layer interposed between the two layers of electrodes are arranged in an array form are known in the related art (for example, refer to JP-A-2010-164331).

In such an ultrasound sensor, a piezoelectric material forming the piezoelectric layer has to be replaced in order to control transmission sensitivity and reception sensitivity. That is, in a case where a dedicated transmission type element and a dedicated reception type element are provided, the elements having different piezoelectric materials have to be arranged, which is very difficult. In a case of unifying the piezoelectric materials, even though the transmission sensitivity and the reception sensitivity are able to be adjusted by varying, for example, a size of an opening portion, it is practically and actually difficult to use since a resonance frequency will be varied according to the varied size of the opening.

The invention was created in consideration of the above-described situation and an object thereof is to provide an ultrasound sensor in which elements having different transmission-reception sensitivity are provided together, without varying the specification of the resonance frequency and a method for manufacturing thereof.

SUMMARY

An aspect of the invention for solving the problems is directed to an ultrasound sensor including: a substrate which has at least one opening portion; a diaphragm which is provided on the substrate so as to block the opening portion; a plurality of first electrodes which is provided so as to be opposite to the opening portion of the diaphragm and to be arranged in a Y-direction, and which extends in a X-direction orthogonal to the Y-direction; a plurality of second electrodes which is provided so as to be opposite to the opening portion of the diaphragm and to be arranged in the X-direction, and which extends in the Y-direction; and a plurality of piezoelectric layers which is provided between the first electrode and the second electrode in at least a portion in which the first electrode and the second electrode intersect with each other, in which, in a Z-direction orthogonal to the X-direction and the Y-direction, a portion in which the first electrode, the piezoelectric layer and the second electrode are overlapped is referred to as an active portion, and a range to the extent that the diaphragm is oscillatable by driving the active portion is referred to as a movable portion, when a unit including one movable portion and the active portion which is provided within the one movable portion is referred to as one ultrasound element in plan view, two or more types of ultrasound elements in which a dimension of the active portion with respect to a dimension of the movable portion is different from each other in plan view are provided.

In the aspect, the ultrasound elements which are optimized to the dedicated transmission type and the dedicated reception type can be provided, transmission and reception can be efficiently performed, and the reliability can be improved by varying a ratio of the active portion to the movable portion without changing a specification of the resonance frequency.

It is preferable that two or more types of ultrasound elements which have the movable portions with the same dimension but the active portions with the different dimension in plan view are provided. Thereby, change in the resonance frequency can be significantly suppressed compared with a case where the dedicated transmission element and the dedicated reception element have the active portions with the same dimension but the movable portions varying in dimension. That is, resonance frequency difference between the elements including the active portions with a dimension different from each other can be reduced. Thereby, it is possible to easily realize the ultrasound sensor having the ultrasound elements which are optimized to the dedicated transmission type and the dedicated reception type with same specification of the resonance frequency.

It is preferable that, in plan view, the opening portions corresponding to the ultrasound elements have the substantially same dimension, the piezoelectric layer corresponding to one opening portion has the same dimension, and any one of the first electrode and the second electrode, corresponding to one opening portion, has different dimension. Thereby, the ultrasound elements which are optimized to the dedicated transmission type and the dedicated reception type can be provided without drastically changing in the manufacturing processes.

It is preferable that the plurality of second electrodes has a width different from each other. According to this configuration, basic manufacturing processes of the ultrasound element do not need to be modified. In a process for forming the second electrodes, the ultrasound elements which are optimized to the dedicated transmission type and the dedicated reception type can be provided only by varying a width of the second electrode when patterning the second electrodes with areas of the dedicated transmission element and the dedicated reception element. Thus, it is possible to obtain the ultrasound sensor having ultrasound elements which are optimized to the dedicated transmission type and the dedicated reception type very easily.

It is preferable that the second electrode has a width different in the X-direction. Thereby, the ultrasound elements having the dedicated transmission element and the dedicated reception element which are optimally arranged can be provided more easily.

It is preferable that the plurality of piezoelectric layers is formed of the substantially same piezoelectric material. According to this configuration, the ultrasound elements which are optimized to the dedicated transmission type and the dedicated reception type can be provided without changing the piezoelectric material. The substantially same material is free of unavoidable or naturally mixed impurities.

Such impurity components are contained with a volume of preferably 3% or less, more preferably 1% or less.

Another aspect of the invention is directed to a method for manufacturing an ultrasound sensor, the method including steps of: forming a diaphragm on a substrate; forming a plurality of first electrodes on the diaphragm so as to be arranged in a Y-direction, which extends in a X-direction orthogonal to the Y-direction; forming a piezoelectric layer on the first electrode; forming a second electrode layer on the diaphragm in which the first electrode and the piezoelectric layer are formed; forming a plurality of the piezoelectric layers and a plurality of second electrodes so as to be arranged in the X-direction, which extend in the Y-direction, by patterning the piezoelectric layer and the second electrode layer; and forming at least one opening portion on a plane opposite to the diaphragm of the substrate, in which, in a Z-direction orthogonal to the X-direction and the Y-direction, a portion in which the first electrode, the piezoelectric layer and the second electrode are overlapped is referred to as an active portion, and a range to the extent that the diaphragm is oscillatable by driving the active portion is referred to as a movable portion, when a unit including one movable portion and the active portion which is provided within the one movable portion is referred to as one ultrasound element in plan view, two or more types of ultrasound elements in which a dimension of the active portion with respect to a dimension of the movable portion is different from each other in plan view are formed by further patterning only the second electrode layer after patterning the piezoelectric layer and the second electrode layer.

In the aspect, the ultrasound elements which are optimized to the dedicated transmission type and the dedicated reception type can be manufactured and transmission performance and reception performance can be improved, respectively, only by varying a dimension of the second electrode (for example, a width of the second electrode) with areas of the dedicated transmission ultrasound element and the dedicated reception ultrasound element when forming the second electrode in a film-manufacturing process and when patterning the second electrode.

DESCRIPTION OF EMBODIMENTS

Figure 1:
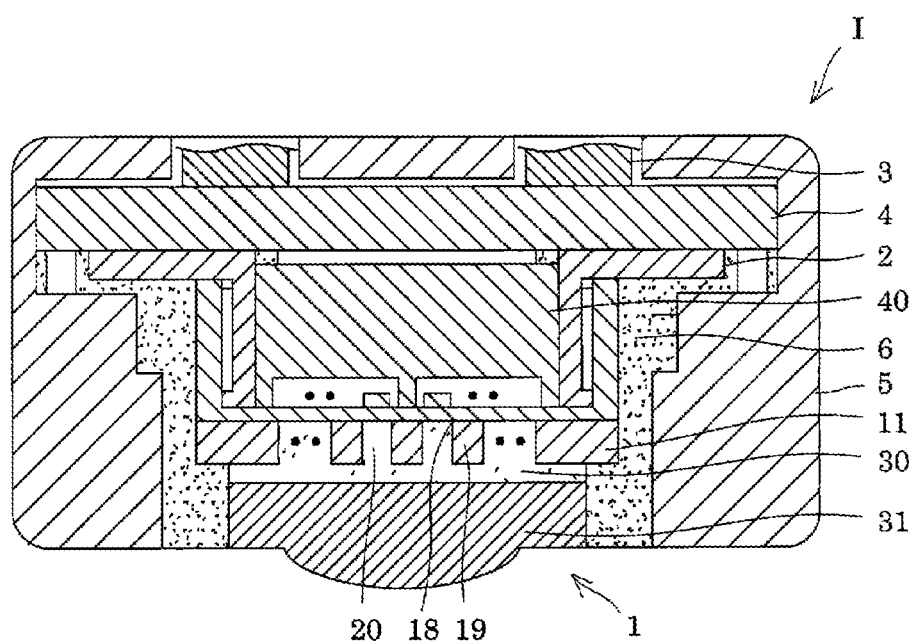
FIG. 1 is a cross-sectional view illustrating a configuration example of an ultrasound device according to Embodiment 1.

Below, embodiments of the invention will be described with reference to the drawings. The description below illustrates one form of the invention, and arbitrary modifications are possible within the scope of the invention. In the respective drawings, portions given the same reference numeral illustrate the same members, and description thereof will not be made, as appropriate.

Embodiment 1

Ultrasound Device FIG. 1 is a cross-sectional view illustrating a configuration example of an ultrasound device on which the ultrasound sensor according to Embodiment 1 of the invention is mounted. As illustrated in FIG. 1, the ultrasound probe I is formed including a CAV surface type ultrasound sensor 1, a flexible printed substrate (FPC substrate 2) connected to the ultrasound sensor 1, a cable 3 drawn out from an apparatus terminal (not shown), a relay substrate 4 that serves as an intermediate between the FPC substrate 2 and the cable 3, a housing 5 that protects the ultrasound sensor 1, the FPC substrate 2 and the relay substrate 4, and a waterproof resin 6 which fills the space between the housing 5 and the ultrasound sensor 1.

Ultrasound waves are transmitted from the ultrasound sensor 1. Ultrasound waves reflected from a measurement target are received by the ultrasound sensor 1. Information (such as position and shape) pertaining to the measurement target is detected in the apparatus terminal of the ultrasound probe I based on the waveform signal of the ultrasound waves.

According to the ultrasound sensor 1, it is possible to ensure high reliability, as described later. Accordingly, by mounting the ultrasound sensor 1, an ultrasound device with various superior characteristics is formed. It is possible to also apply the invention to any ultrasound sensor 1, such as a dedicated transmission type optimized to the transmission of ultrasound waves, a dedicated reception type optimized to the reception of ultrasound waves, and a transmission and reception integrated type optimized to the transmission and reception of ultrasound waves. The ultrasound device on which the ultrasound sensor 1 is able to be mounted is not limited to the ultrasound probe I.

Figure 2:
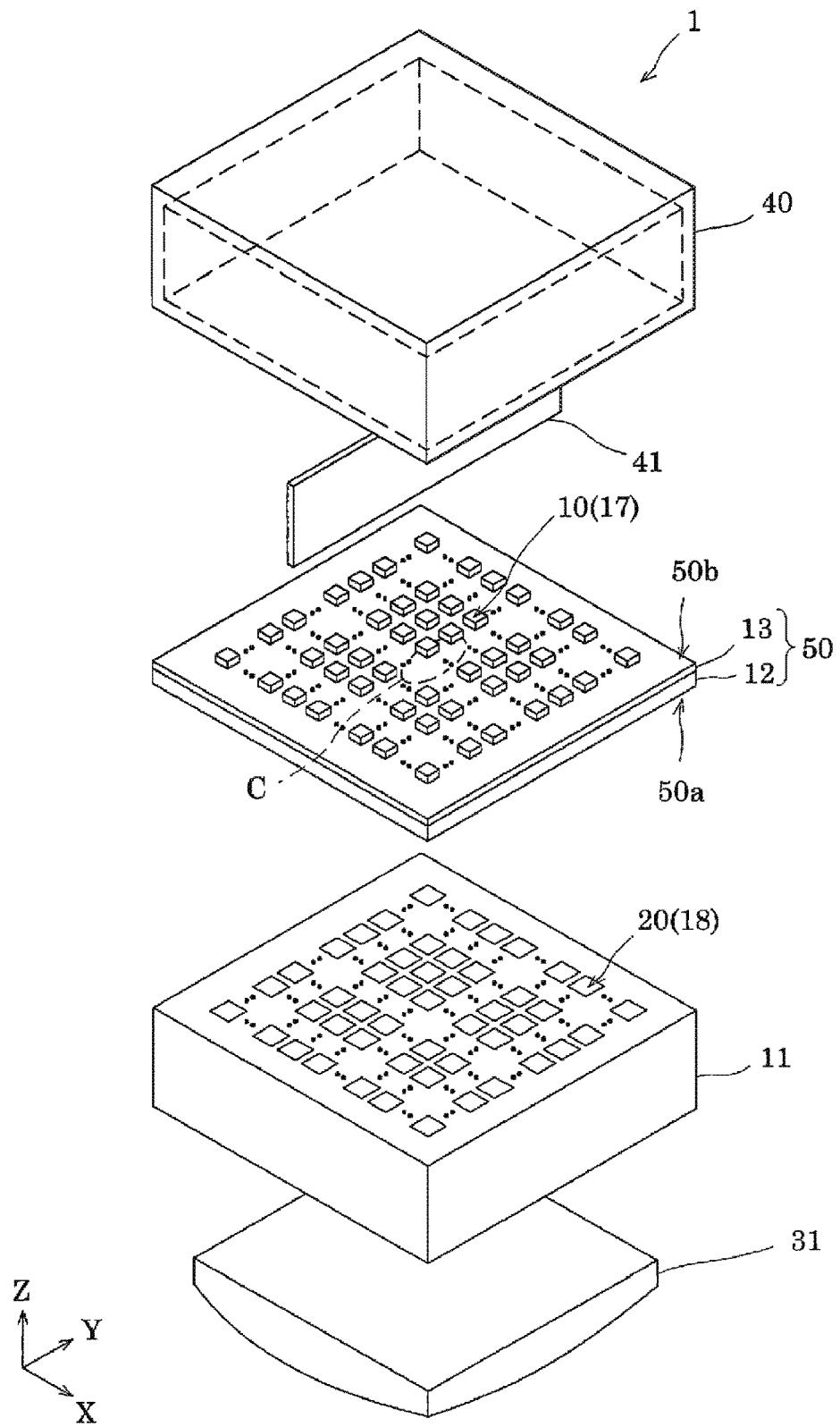
FIG. 2 is an exploded perspective view illustrating a configuration example of an ultrasound sensor according to Embodiment 1.
Figure 3:
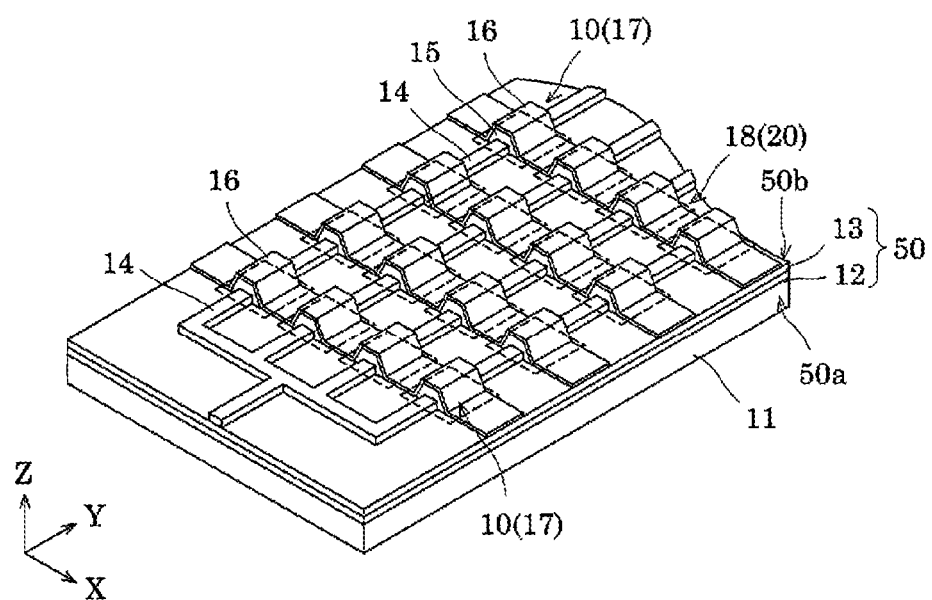
FIG. 3 is an enlarged perspective view illustrating a configuration example of an ultrasound element array.
Figure 4:
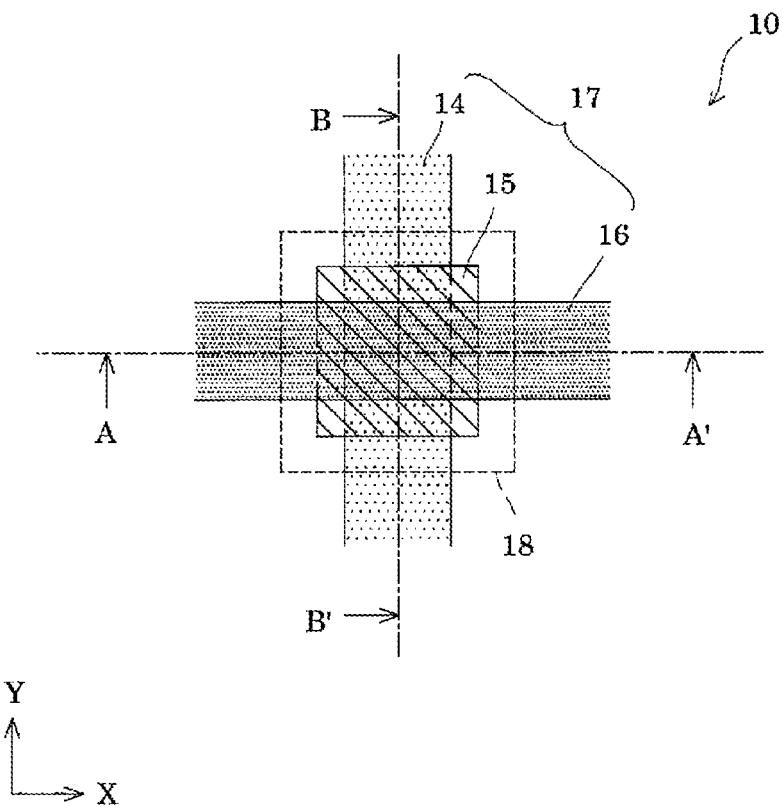
FIG. 4 is a plan view illustrating a schematic configuration of the ultrasound sensor element according to Embodiment 1.
Figure 5A:
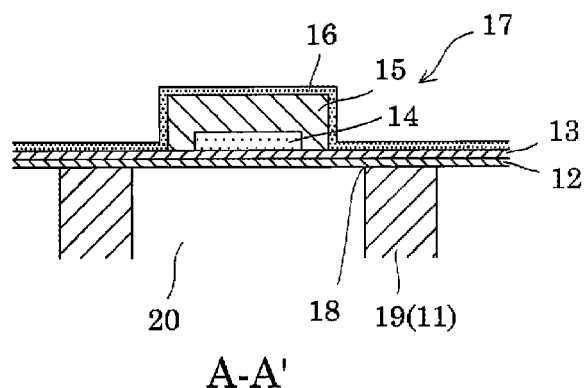
FIGS. 5A and 5B show cross-sections of the ultrasound sensor element according to Embodiment 1.
Figure 5B:
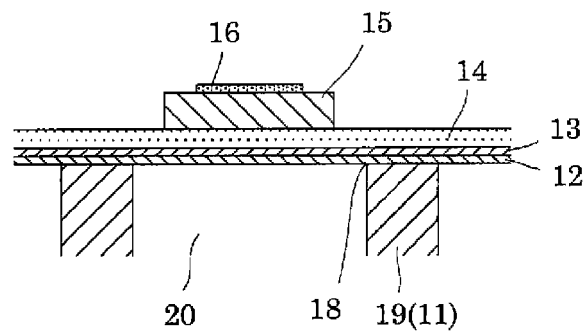
Figure 6:
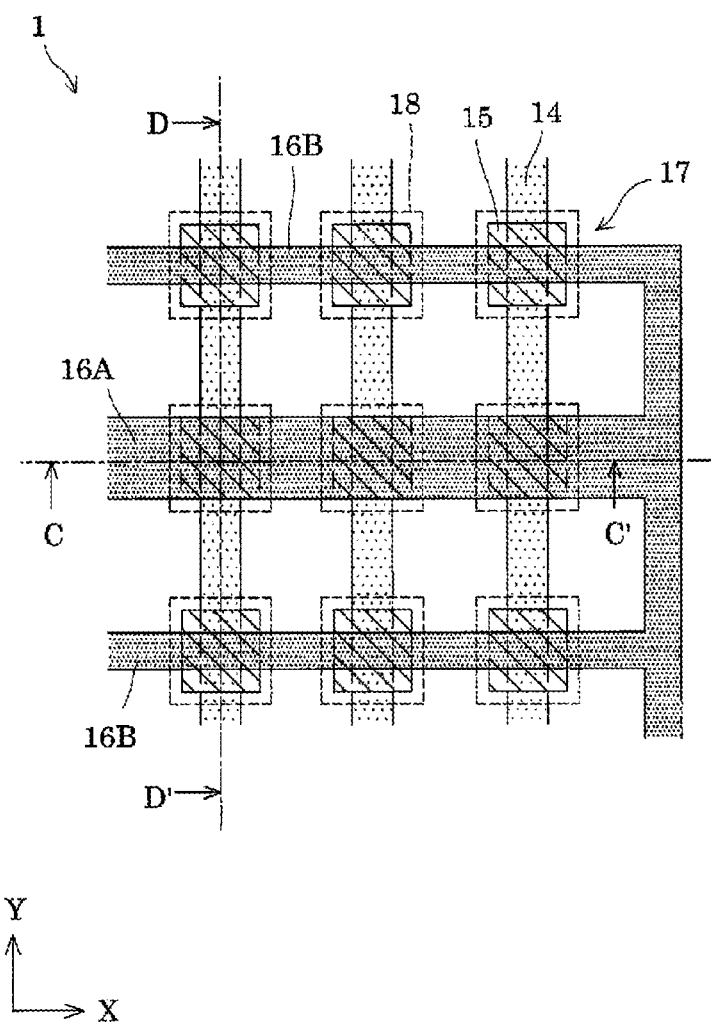
FIG. 6 is a plan view illustrating a schematic configuration of the ultrasound sensor according to Embodiment 1.
Figure 7A:
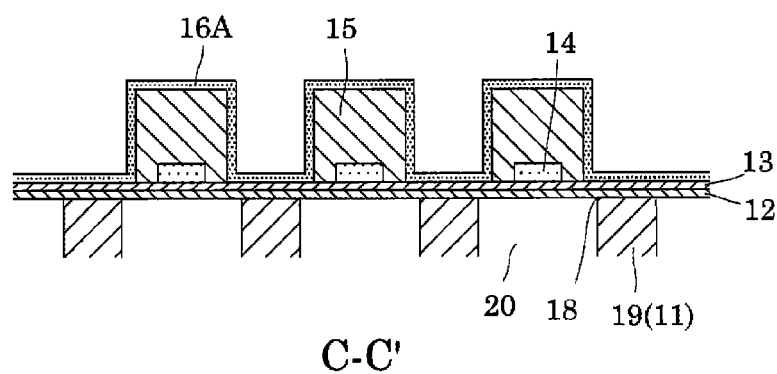
FIGS. 7A and 7B show cross-sections of the ultrasound sensor according to Embodiment 1.
Figure 7B:
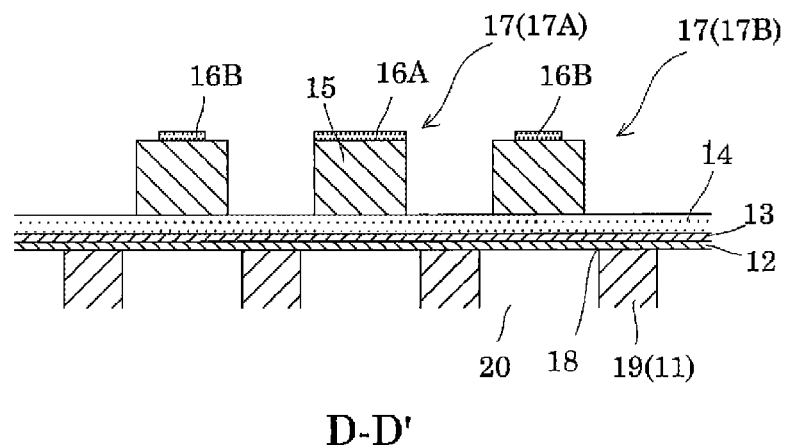

Ultrasound Sensor FIG. 2 is an exploded perspective view of the ultrasound sensor. FIG. 3 is an enlarged perspective view illustrating a configuration example of an ultrasound sensor element array. FIG. 4 is a plan view of the ultrasound sensor element configuring the ultrasound sensor according to Embodiment 1 of the invention, FIGS. 5A and 5B show a cross-sectional view taken along line A-A' and a cross-sectional view taken along line B-B', FIG. 6 is a plan view illustrating a schematic configuration of the ultrasound sensor, FIGS. 7A and 7B show a cross-sectional view taken along line C-C', and a cross-sectional view taken along line D-D'.

The ultrasound sensor 1 is formed including an ultrasound element 10, an acoustic matching layer 30, a lens member 31, and an enclosure plate 40. The ultrasound element 10 is formed including a substrate 11, a diaphragm 50, and a piezoelectric element 17. In FIG. 2, although the enclosure plate 40 and the support member 41 are depicted as separate bodies, in practice, both are integrally formed.

When two mutually orthogonal axes are the X-axis and the Y-axis and the plane formed by the X-axis and the Y-axis is the XY-plane, the substrate 11 follows the XY-plane. Below, the X-axis is referred to as the first direction X, the Y-axis as the second direction Y, and the Z-axis direction which is orthogonal to both of the first direction X and the second direction Y as the third direction Z.

A plurality of dividing walls 19 are formed on the substrate 11. A plurality of spaces 20 are divided along the first direction X and the second direction Y by the plurality of dividing walls 19. The spaces 20 are formed so as to pass through the substrate 11 in the third direction Z. The spaces 20 are formed in a two-dimensional form, that is, a plurality in the first direction X and a plurality in the second direction Y. The arrangement or shape of the spaces 20 can be modified in various ways. For example, the spaces 20 may also be formed in a one-dimensional form, that is, along one direction of either of the first direction X and the second direction Y. The spaces 20 may also have a long shape (a ratio of lengths in the first direction X and the second direction Y other than 1:1) when viewed from the third direction Z.

The diaphragm 50 is provided on the substrate 11 so as to block an opening portion 18 formed of the space 20. Below, the surface on the substrate 11 side of the diaphragm 50 is referred to as a first surface 50a, and the surface facing the first surface 50a is referred to as a second surface 50b. The diaphragm 50 is formed of an elastic film 12 formed on the substrate 11 and an insulator film 13 formed on the elastic film 12. In this case, the first surface 50a is formed of the elastic film 12 and the second surface 50b of the insulator film 13.

Hereinafter, the ultrasound element will be described in detail.

As illustrated in drawing, the ultrasound element 10 of the embodiment is formed of an elastic film 12 formed of a silicon dioxide film provided on one surface of the substrate 11 formed of a silicon substrate and the piezoelectric element 17 which is formed on the insulator film 13 formed of zirconium oxide and which formed of a first electrode 14, a piezoelectric layer 15, and a second electrode 16. The opening portion 18 is formed in a region corresponding to the piezoelectric element 17 of the substrate 11, and the space 20 forming the opening portion 18 is divided by the dividing wall 19.

Although it is possible to use a single-crystal silicon substrate as the substrate 11, there is no limitation thereto. In the embodiment, although the diaphragm is configured by the elastic film 12 formed of silicon dioxide or the like and the insulator film 13 formed of zirconium oxide or the like, there is no limitation thereto, and either one may be used or another film may be used.

The piezoelectric element 17, which is formed of the first electrode 14, the piezoelectric layer 15 with a thin film thickness of 3 μm or less and preferably 0.3 μm to 1.5 μm, and the second electrode 16 with an adhesive layer interposed as necessary, is formed on the insulator film 13. Here, the piezoelectric element 17 refers to the portion that contains the first electrode 14, the piezoelectric layer 15, and the second electrode 16. A region interposed between the first electrode 14 and the second electrode 16 is referred to an active portion.

In general, in a case of driving the piezoelectric element 17, although either one of the electrodes is a common electrode and the other electrode is an individual electrode, in the ultrasound element 10, since driving and scanning are performed for each plurality of ultrasound elements 10, it is not realistic to distinguish which one is the common electrode and which is the individual electrode. In any case, in a case of using a form in which the ultrasound elements 10 are arranged one-dimensionally or two-dimensionally, it is possible to drive only a predetermined piezoelectric element 17 by providing the first electrode 14 so as to span in one direction, provide the second electrode 16 so as to span in a direction orthogonal to the one direction, and applying a voltage between the first electrode 14 and the second electrode 16 selected, as appropriate. When selecting the predetermined piezoelectric element 17, the driving is generally performed by selecting one row or a plurality of rows as one group. In the embodiment, four rows of the first electrodes 14 are bound and shared. This is tentatively referred to as 1-channel, and a plurality of channels are provided spanning the first direction X. The second electrode 16 is continuously provided as one row along the first direction X, and a plurality of rows is provided along the second direction Y.

In such a configuration, when all rows of the second electrodes 16 are shared, all of the piezoelectric elements 17 in the 1-channel are driven at the same time and each channel is driven sequentially, it is possible to acquire data of one dimension along the first direction X.

When the second electrodes 16 are shared one row at a time or a plurality of rows at a time, the piezoelectric elements 17 in 1-channel are shared by the second electrodes 16 and sequentially driven a group at a time, and each channel is sequentially driven, it is possible to acquire two-dimensional data in the XY direction.

Hereafter, the combination of the piezoelectric element 17, and the elastic film 12 and the insulator film 13 which are the diaphragm 50 in which displacement occurs due to driving of the piezoelectric element 17 are referred to as an actuator apparatus. In the above-described examples, although the elastic film 12 and the insulator film 13, the adhesive layer which is provided as necessary, and the first electrode 14 act as the diaphragm 50, there is no limitation thereto. For example, the diaphragm 50 need not be provided, and the piezoelectric element 17 itself may substantially serve as the diaphragm 50.

In the piezoelectric element 17, the active portion indicates a portion in which the first electrode 14, the piezoelectric layer 15 and the second electrode 16 are overlapped in plan view and also a region in which the piezoelectric layer 15 is interposed between the first electrode 14 and the second electrode 16. Furthermore, the movable portion refers to a region in which the first electrode 14 and the second electrode 16, in addition to the elastic film 12 and the insulator film 13, also serve as the diaphragm 50 blocking the opening portion 18 and which corresponds to the opening portion 18 of the diaphragm 50, i.e. a region in which the diaphragm 50 can be oscillated by driving the piezoelectric element 17. The active portion corresponds to the movable portion one-to-one. In the present embodiment, the active portion corresponds to the opening portion 18 one-to-one. However, one opening portion 18 may contain a plurality of the active portions in plan view. In this case, the active portion can substantially correspond to the movable portion one-to-one by providing, for example, a columnar partition, which suppresses the oscillation of the diaphragm 50, between the neighboring active portions and limiting a region in which the diaphragm 50 can be oscillated within the opening portion 18.

The first electrode 14 and the second electrode 16 are not limited as long as they have conductivity and it is possible to use metal materials, such as platinum (Pt), iridium (Ir), gold (Au), aluminum (Al), copper (Cu), titanium (Ti), and stainless steel; tin oxide-based conductive materials, such as indium tin-oxide (ITO), and fluorine-doped tin oxide (FTO); zinc-oxide-based conductive materials, conductive oxides, such as strontium ruthenate (SrRuO3), lanthanum nickelate (LaNiO3), element doped strontium titanate; and conductive polymers. However, there is no restriction to these materials.

It is possible to use a complex oxide with a lead zirconate titanate (PZT)-based perovskite structure for the piezoelectric layer 15, as a representative. Thereby, the displacement amount of the piezoelectric element 17 is easily ensured.

The piezoelectric layer 15 does not include lead, and, for example, it is possible to use a complex oxide with a perovskite structure which includes at least bismuth (Bi), barium (Ba), iron (Fe), and titanium (Ti). Thereby, it is possible to realize an ultrasound element 10 using a non-lead based material with a low load on the environment.

The A site of such a perovskite structure, that is, an ABO3 type structure, is coordinated with 12 oxygen atoms, and, in addition, the B site is coordinated with 6 oxygen atoms, thereby forming an octahedron. In the example of the above-described piezoelectric layer 15 which does not contain lead, the Bi, Ba, and Li are positioned at the A site and the Fe and Ti at the B site.

In the complex oxide which includes a perovskite structure including Bi, Ba, Fe, and Ti, although the constitution formula is represented by (Bi, Ba) (Fe, Ti)$O_3$, a representative constitution is represented as a mixed crystal of bismuth ferrate and barium titanate. The bismuth ferrite and barium titanate of the mixed crystal are not detected singly in an X-ray diffraction pattern. Constitutions deviating from the constitution of the mixed crystal are also included.

Constitutions shifted from the stoichiometric constitution due to lack or excess or in which a portion of the elements are substituted with other elements are also included in the complex oxide with a perovskite structure. That is, as long as a perovskite structure is obtainable, the inevitable deviations in the constitution due to lattice mismatching, oxygen faults and the like such as partial substitution of elements are naturally also permissible.

The configuration of the complex oxide with a perovskite structure is not limited to the examples, and the configuration may include other elements. It is preferable that the piezoelectric layer 15 further include manganese (Mn). Thereby, leakage current is suppressed and it is possible to realize a high-reliability ultrasound element 10 as a non-lead based material.

Bi at the A site of the piezoelectric layer 15 may be substituted with lithium (Li), samarium (Sm), cerium (Ce) or the like, and the Fe at the B site may be substituted with aluminum (Al), cobalt (Co), and the like. Thereby, various characteristics are improved, thereby easily achieving diversification of the configuration and function. Even in the case of a compound oxide including these other elements, it is preferable that the configuration have a perovskite structure.

As illustrated in FIG. 6, the ultrasound elements 10 of the ultrasound sensor 1 of the present embodiment are arranged two-dimensionally in the first direction X and the second direction Y orthogonal thereto, and the first direction X and the second direction Y are the scanning direction and the slice direction, respectively. In such an ultrasound sensor 1, it is possible to continuously acquire, in the scanning direction, sensing information in the slice direction by performing driving, that is, performing transmission and reception of ultrasonic waves for each row extending in the slice direction while scanning in the scanning direction.

In the present embodiment, the elements are assigned to the dedicated transmission type and the dedicated reception type for one row extended in the first direction X at a time. That is, as illustrated in FIG. 7, the piezoelectric layer 15 and a second electrode 16A have the same width in a center row, while the second electrode 16B has a narrower width than that of the piezoelectric layer 15 in rows on both sides. The piezoelectric layers 15 and the opening portion 18 share the same width, and a second electrode 16B is narrower than the second electrode 16A in any of the rows.

In such ultrasound sensor 1, the movable portion when the piezoelectric element 17 is driven corresponds to a dimension of the opening portion 18. In a center piezoelectric element 17A, the active portion, i.e. a region in which the piezoelectric layer 15 is interposed between the first electrode 14 and the second electrode 16, has a dimension different from that of the active portions in a piezoelectric elements 17B on both sides. The active portions in the piezoelectric elements on both sides are smaller.

If the dimension of the active portion is changed by varying the width of the second electrode 16 only, the transmission characteristic and the reception characteristic can be changed while the change in resonance frequency (resonance frequency difference) is drastically suppressed. The transmission characteristic (transmission sensitivity) is proportional to an excluded volume v due to the displacement of the movable portion based on driving of the active portion. The excluded volume v is proportional to a dimension S of the active portion. That is, the larger the dimension S of the active portion is, the better the transmission characteristic is. Furthermore, in the present embodiment, the reception characteristic (reception sensitivity) is evaluated based on voltage generated by the reception. The generated voltage V is represented by V=Q/C (Q indicates generated charge and C indicates a capacitance) and is inversely proportional to the capacitance of the piezoelectric element. The capacitance C is represented by ε0×εr×(S/t) (ε0 indicates a vacuum permittivity, εr indicates a relative permittivity of the piezoelectric element, S indicates the dimension of the active portion and t indicates a thickness of the piezoelectric element (active portion)). The smaller the dimension S of the active portion is, the smaller the capacitance C is. That is, the reception characteristic is improved but the transmission characteristic is deteriorated as the width of the second electrode 16 becomes narrower. The transmission characteristic is improved but the reception characteristic is deteriorated as the width of the second electrode 16 becomes wider. Thus, the center piezoelectric element 17A acts as the dedicated transmission element, and the piezoelectric elements 17B on both sides act as the dedicated reception elements. This configuration allows both transmission characteristic and reception characteristic to be improved. Moreover, the dedicated reception element and the dedicated transmission element are provided with the active portions having different dimensions but the movable portions having the same dimension, the resonance frequency difference between them is extremely small. Therefore, transmission and reception can be efficiently performed without varying in a specification of the resonance frequency in the dedicated reception element and the dedicated transmission element.

Hereinafter, examples of a method for manufacturing the ultrasound sensor of Embodiment 1 will be described with reference to FIGS. 8 to 13. Each of these drawings illustrates each process and includes a plan view and cross-sectional views taken along lines b-b' and c-c'.

Figure 8A:
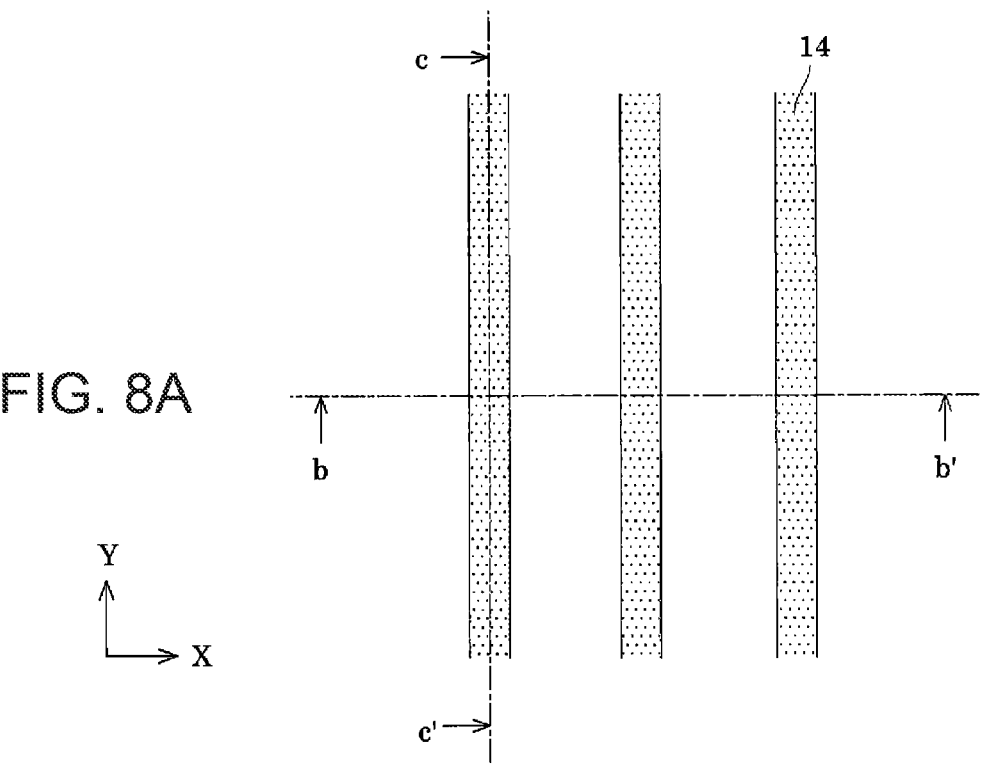
FIGS. 8A, 8B and 8C show a plan view and a cross-sectional view illustrating a manufacturing example of the ultrasound sensor according to Embodiment 1.
Figure 8B:
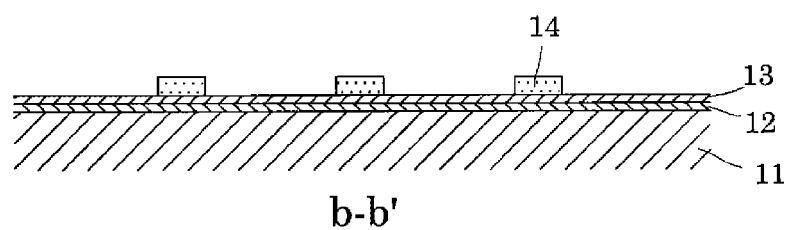
Figure 8C:
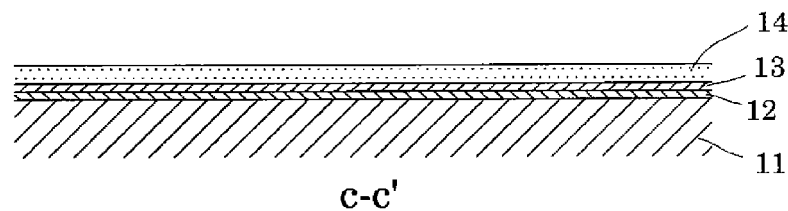

First, as illustrated in FIGS. 8A, 8B and 8C, after forming an elastic film 12 formed of silicon oxide by thermal oxidation or the like of the substrate 11, a zirconium film is formed thereupon, and thermally oxidized at 500 to 1200° C., and the insulator film 13 formed of zirconium oxide is formed. The first electrode 14 is formed on the insulator film 13 by a sputtering method, a deposition method or the like, and patterning carried out so that the first electrode 14 takes a predetermined shape.

Figure 9A:
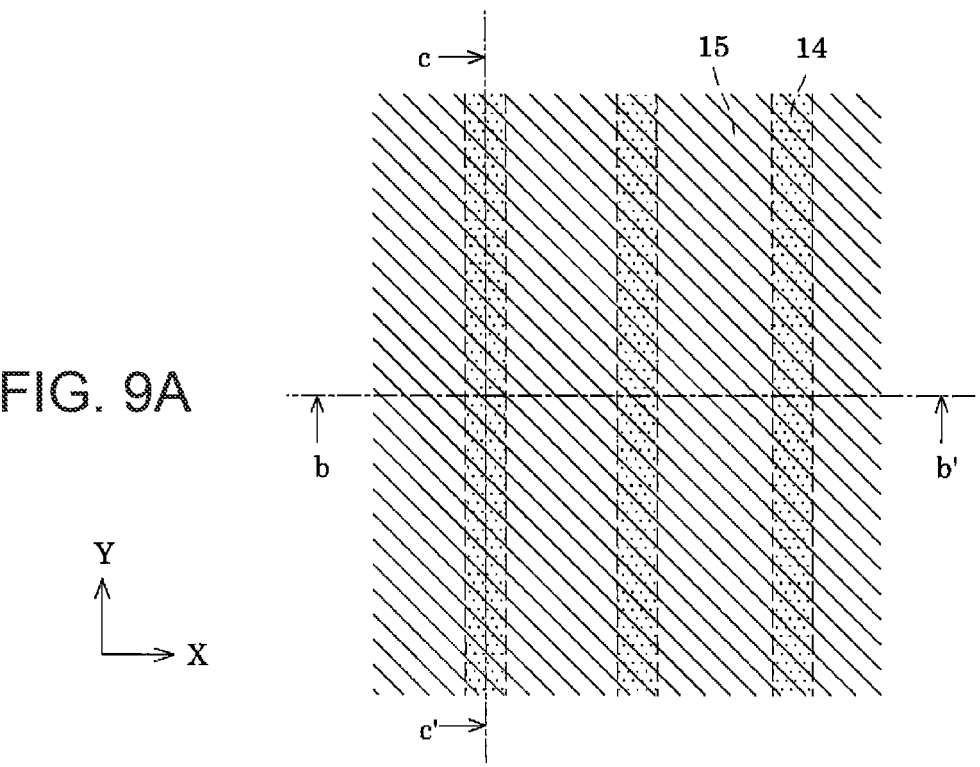
FIGS. 9A, 9B and 9C show a plan view and a cross-sectional view illustrating a manufacturing example of the ultrasound sensor according to Embodiment 1.
Figure 9B:
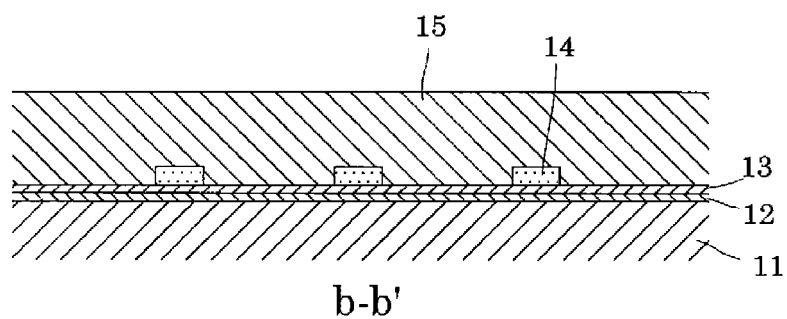
Figure 9C:
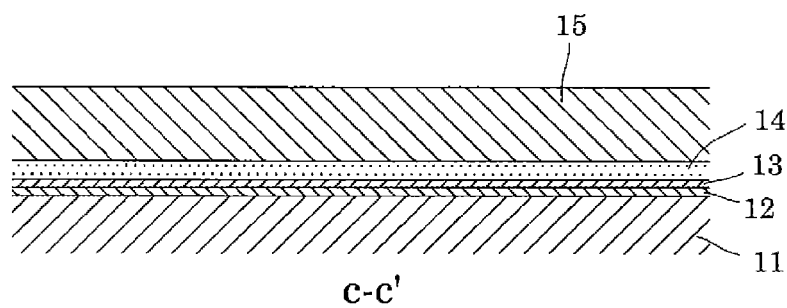

Next, as illustrated in FIGS. 9A, 9B and 9C, the piezoelectric layer 15 is layered on the first electrode 14 and patterning carried out. It is possible to form a piezoelectric layer 15 using a chemical solution deposition (CSD) method in which a piezoelectric material formed of a metal oxide is obtained by coating and drying a metal complex is in which a metal complex is dissolved and dispersed in a solvent and further baking at a high temperature. There is no limitation to the CSD method, and a sol-gel method, a laser ablation method, a sputtering method, a pulse laser deposition method (PLD method), a CVD method, an aerosol deposition method and the like may be used.

Figure 10A:
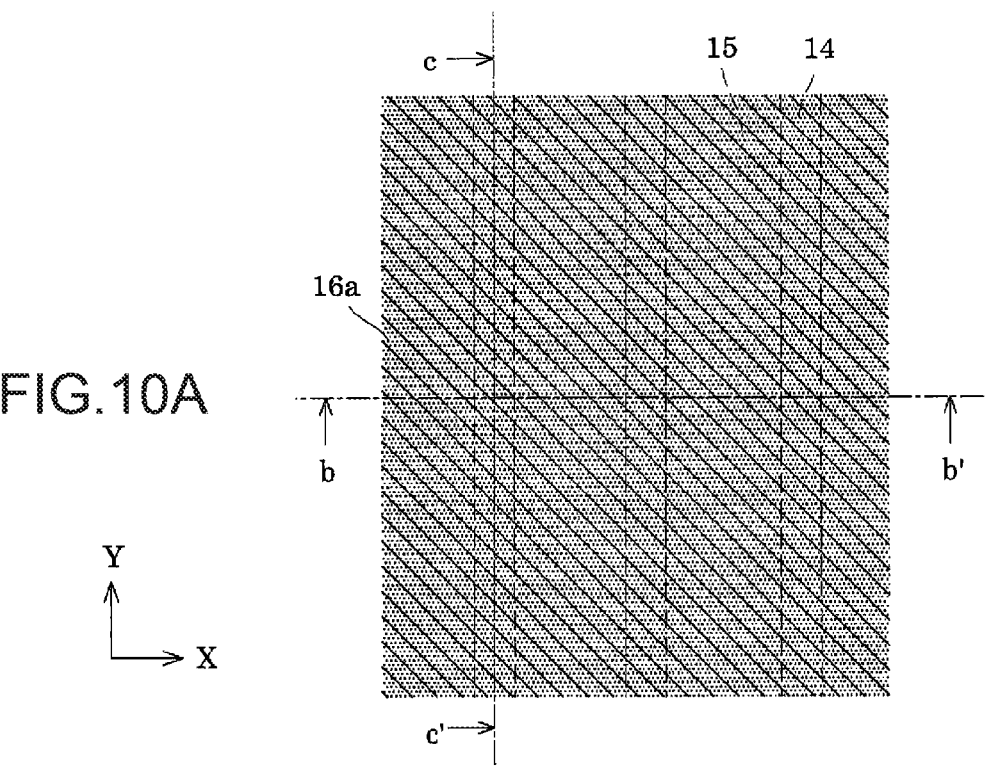
FIGS. 10A, 10B, and 10C show a plan view and a cross-sectional view illustrating a manufacturing example of the ultrasound sensor according to Embodiment 1.
Figure 10B:
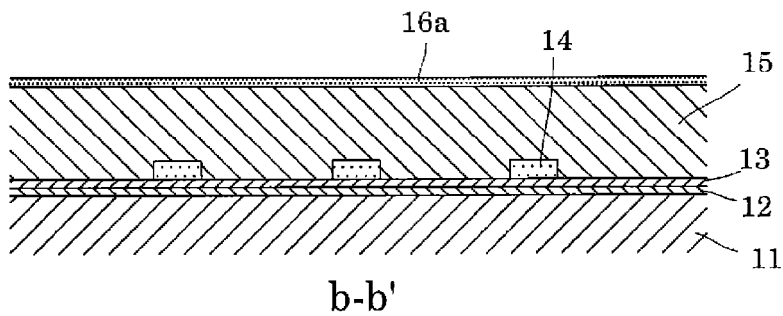
Figure 10C:
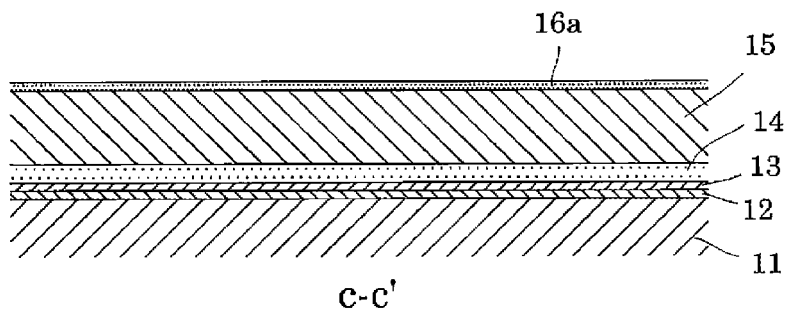
Figure 11A:
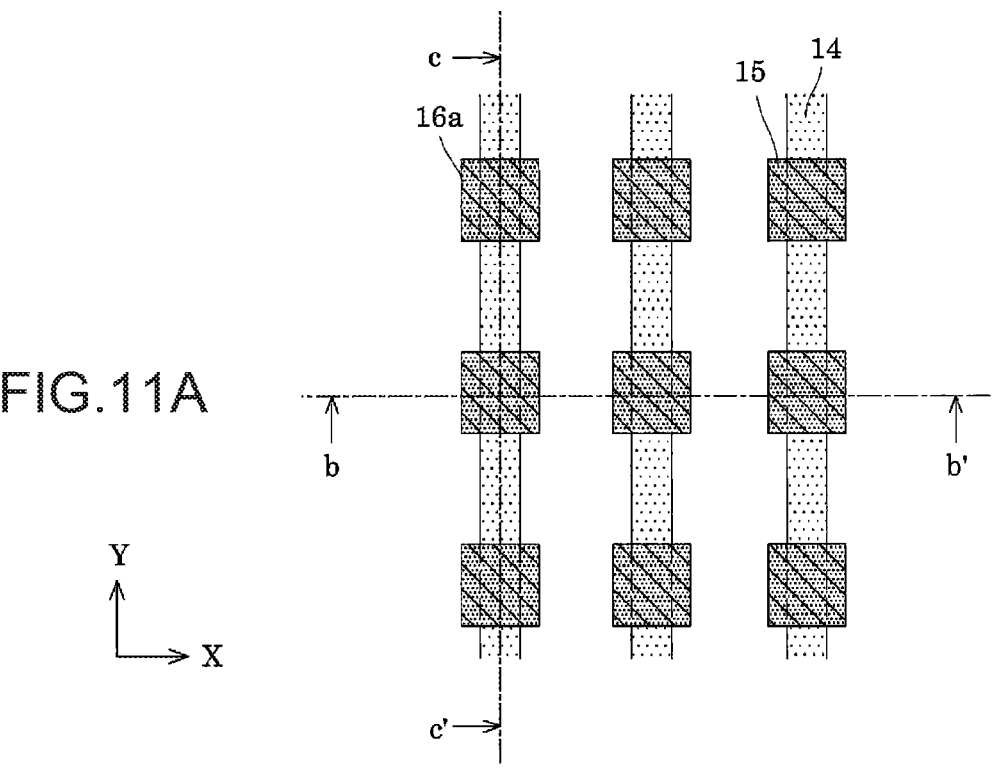
FIGS. 11A, 11B, and 11C show a plan view and a cross-sectional view illustrating a manufacturing example of the ultrasound sensor according to Embodiment 1.
Figure 11B:
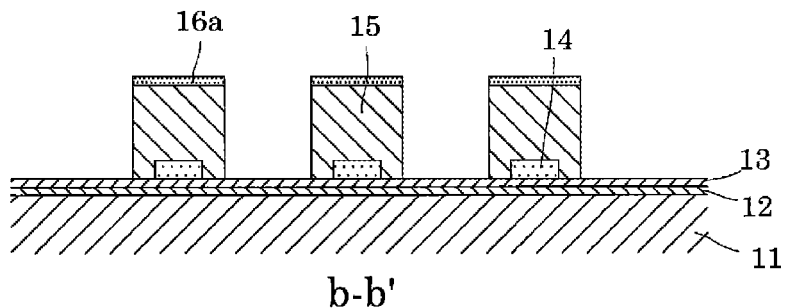
Figure 11C:
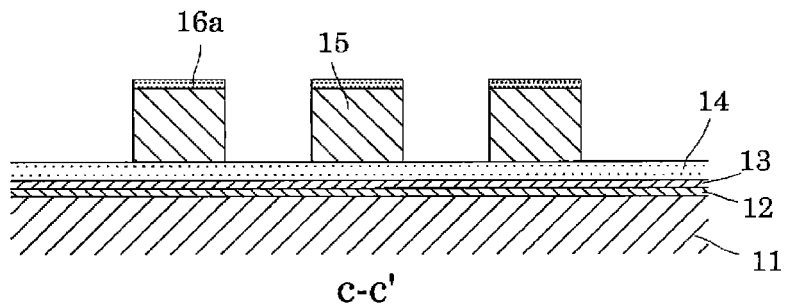

Next, as illustrated in FIGS. 10A, 10B and 10C, the primary second electrode 16a is formed by a sputtering method, a thermal oxidation method or the like on the piezoelectric layer 15 and, as illustrated in FIGS. 11A, 11B and 11C, the primary second electrode 16a and the piezoelectric layer 15 are subjected to patterning for each piezoelectric element.

Figure 12A:
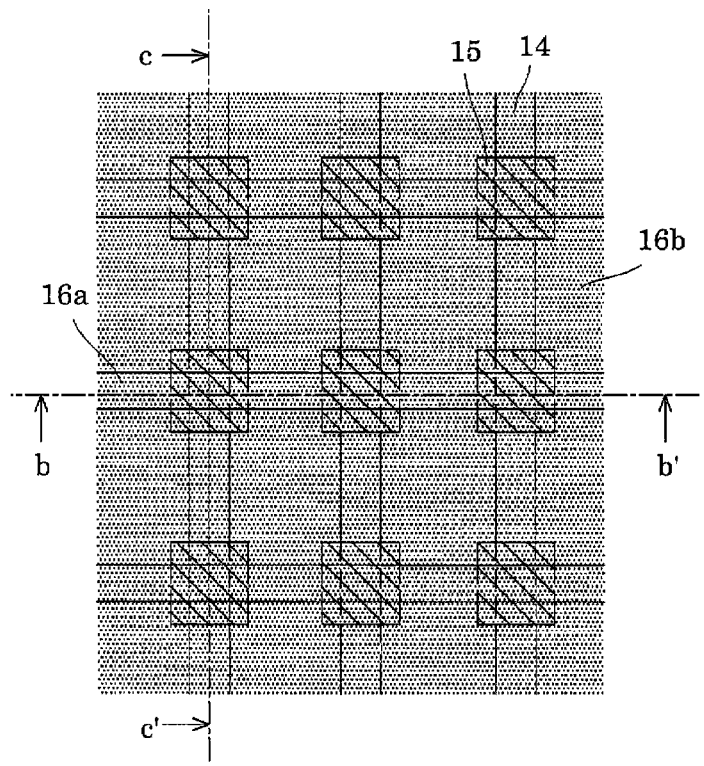
FIGS. 12A, 12B and 12C show a plan view and a cross-sectional view illustrating a manufacturing example of the ultrasound sensor according to Embodiment 1.
Figure 12B:
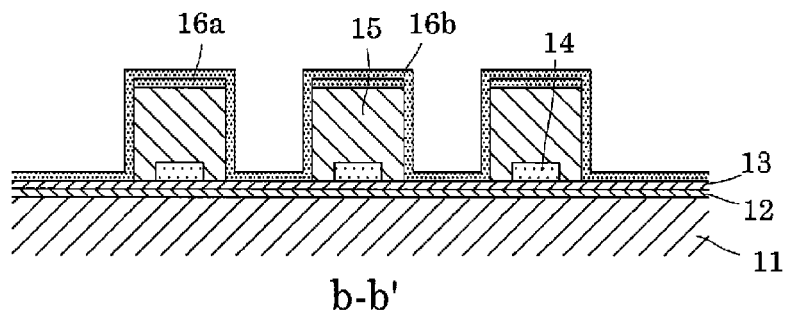
Figure 12C:
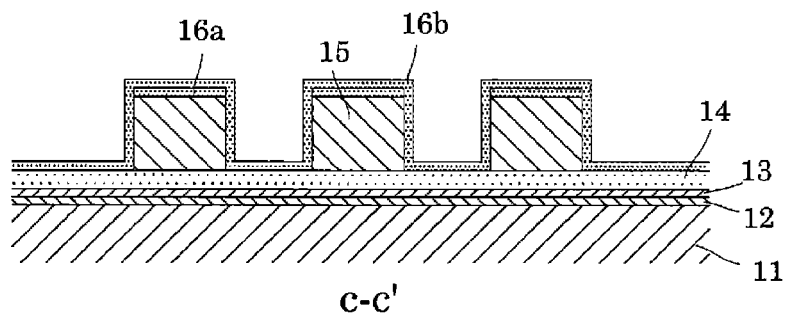
Figure 13A:
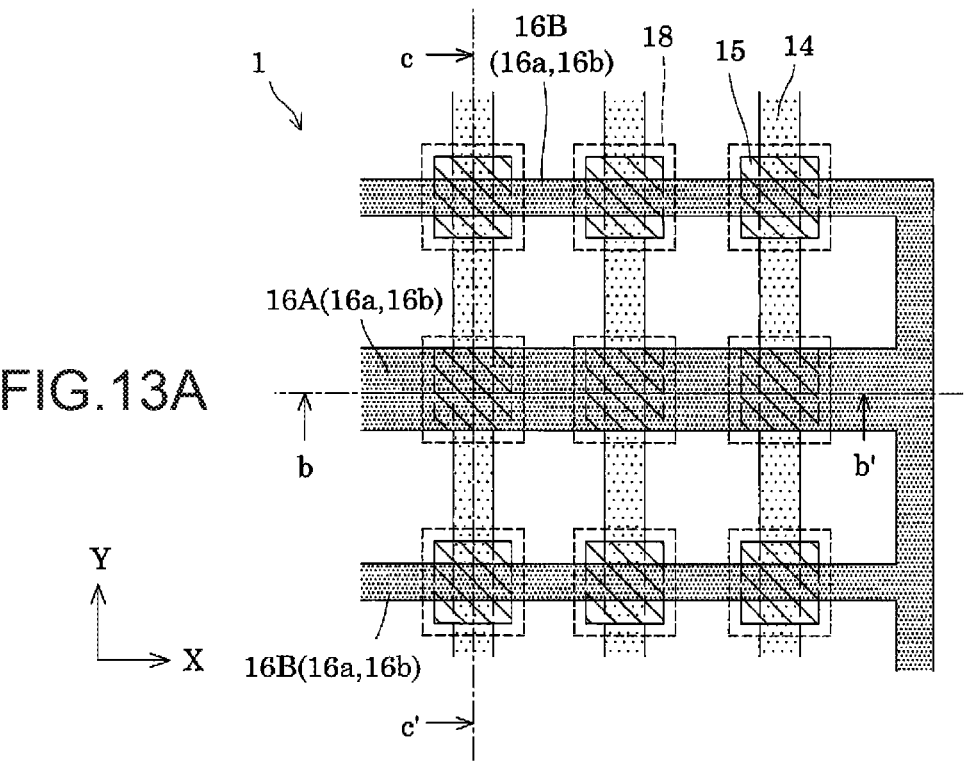
FIGS. 13A, 13B and 13C show a plan view and a cross-sectional view illustrating a manufacturing example of the ultrasound sensor according to Embodiment 1.
Figure 13B:
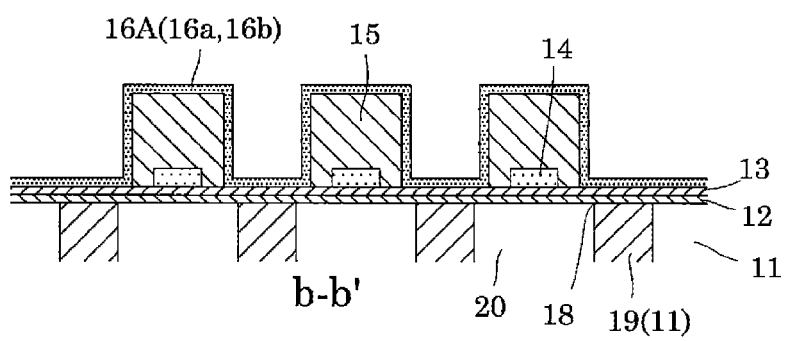
Figure 13C:
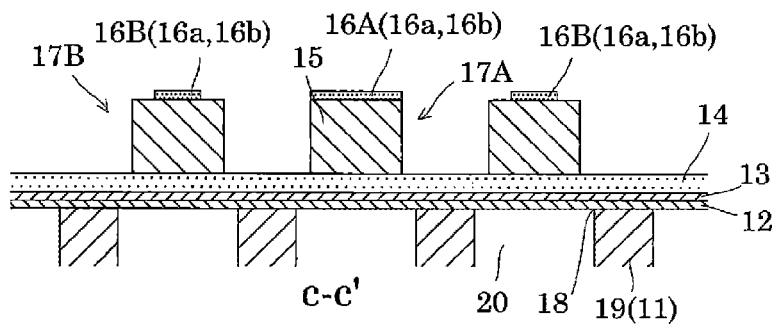

Next, as illustrated in FIGS. 12A, 12B and 12C, the secondary second electrode 16b is provided in the same manner of the primary second electrode 16a. As illustrated in FIGS. 13A, 13B and 13C, the primary second electrode 16a and the secondary second electrode 16b are subjected to patterning and divided for each row in the second direction Y such that they are continuously arranged for each row in the first direction X. In the center raw of the drawing, the second electrode 16A is wider, of which width is the approximately same as that of the piezoelectric layer 15. In the rows on both sides, the narrower second electrodes 16B are provided. With this configuration, the dedicated transmission piezoelectric element 17A having the wider second electrode 16A and the dedicated reception piezoelectric element 17B having the narrower second electrode 16B are formed.

Subsequently, a protective film is formed and subjected to patterning as appropriate, and then the opening portion is formed. Thereby, the ultrasound sensor 1 is obtained.

As described above, the dedicated transmission piezoelectric element 17A and the dedicated reception piezoelectric element 17B can be manufactured and transmission performance and reception performance can be improved, respectively, only by varying the patterning of the secondary second electrode 16b, which is performed in a last stage of the film-forming process of the ultrasound sensor 1.

Embodiment 2

An ultrasound sensor 1A of Embodiment 2 will be described with reference to one example of the manufacturing method. Each of FIGS. 14 to 19 illustrates each process and includes a plan view and cross-sectional views taken along lines b-b' and c-c'. In Embodiment 1 stated above, the second electrode 16 is a common electrode, but in Embodiment 2, the first electrode 14 is a common electrode.

Figure 14A:
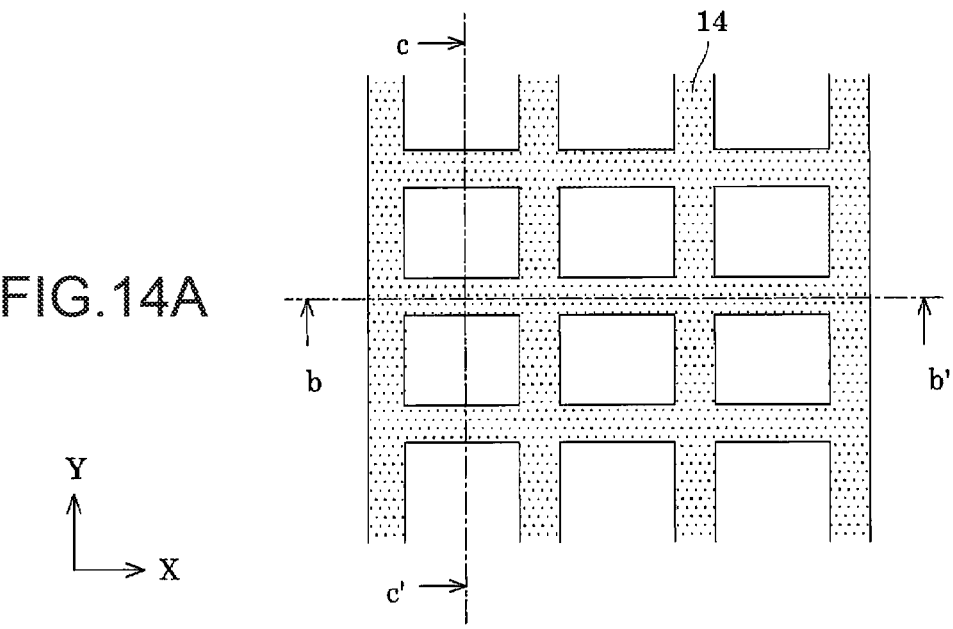
FIGS. 14A, 14B, and 14C show a plan view and a cross-sectional view illustrating a manufacturing example of the ultrasound sensor according to Embodiment 2.
Figure 14B:
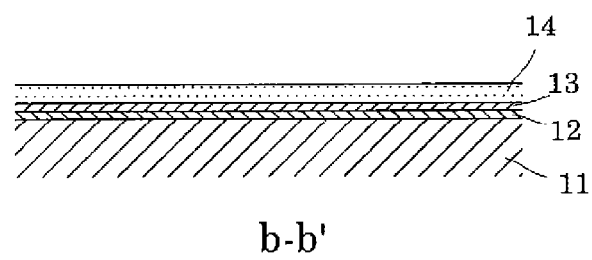
Figure 14C:
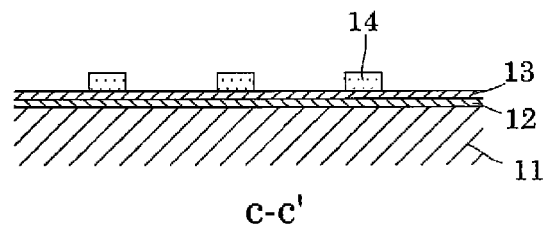

First, as illustrated in FIGS. 14A, 14B and 14C, after forming an elastic film 12 formed of silicon oxide by thermal oxidation or the like of a substrate 11, a zirconium film is formed thereupon, and thermally oxidized at 500 to 1200° C., and an insulator film 13 formed of zirconium oxide is formed. The first electrode 14 is formed on the insulator film 13 by a sputtering method, a deposition method or the like, and patterning carried out so that the first electrode 14 takes a predetermined shape.

Figure 15A:
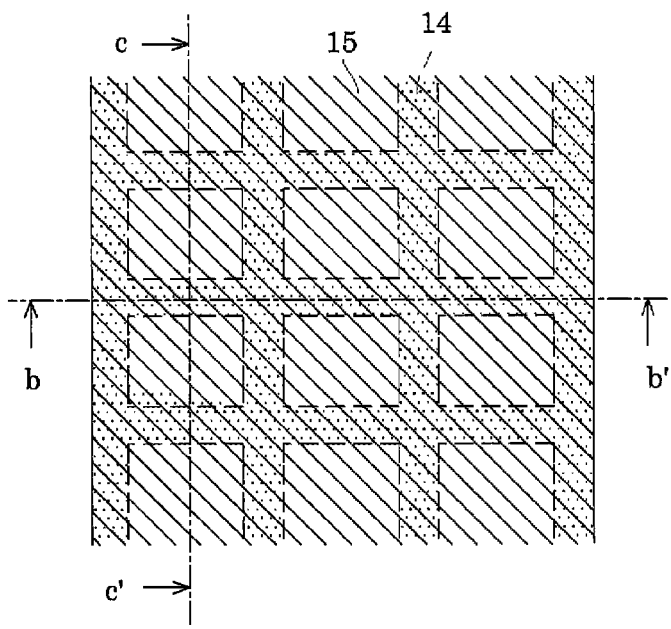
FIGS. 15A, 15B and 15C show a plan view and a cross-sectional view illustrating a manufacturing example of the ultrasound sensor according to Embodiment 2.
Figure 15B:
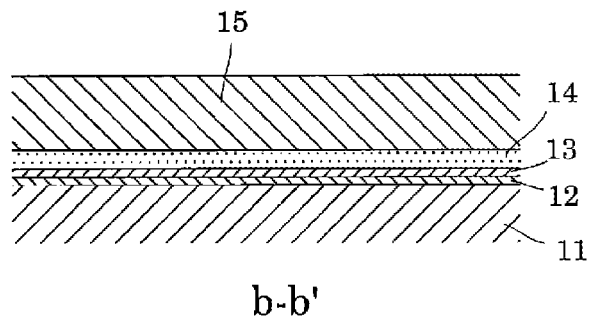
Figure 15C:
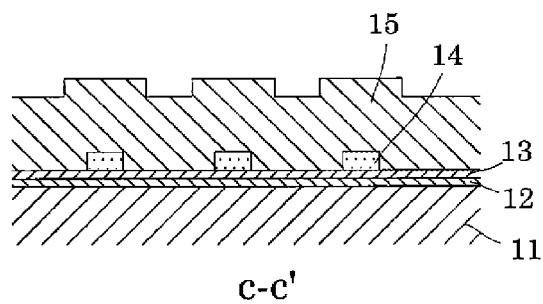

Next, as illustrated in FIGS. 15A, 15B and 15C, the piezoelectric layer 15 is layered on the first electrode 14 and patterning carried out. It is possible to form a piezoelectric layer 15 using a chemical solution deposition (CSD) method in which a piezoelectric material formed of a metal oxide is obtained by coating and drying a metal complex is in which a metal complex is dissolved and dispersed in a solvent and further baking at a high temperature. There is no limitation to the CSD method, and a sol-gel method, a laser ablation method, a sputtering method, a pulse laser deposition method (PLD method), a CVD method, an aerosol deposition method and the like may be used.

Figure 16A:
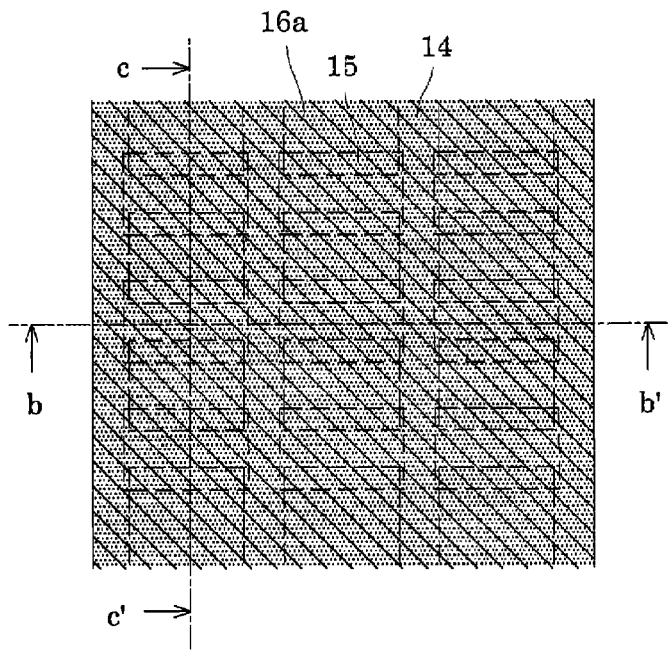
FIGS. 16A, 16B and 16C show a plan view and a cross-sectional view illustrating a manufacturing example of the ultrasound sensor according to Embodiment 2.
Figure 16B:
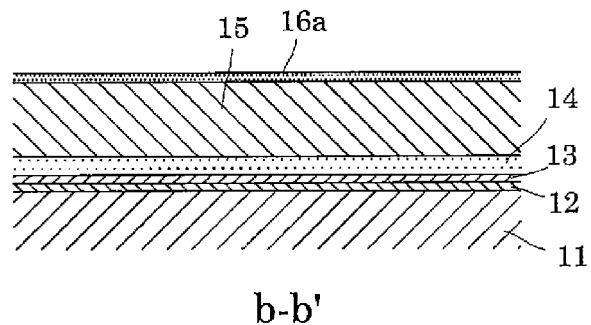
Figure 16C:
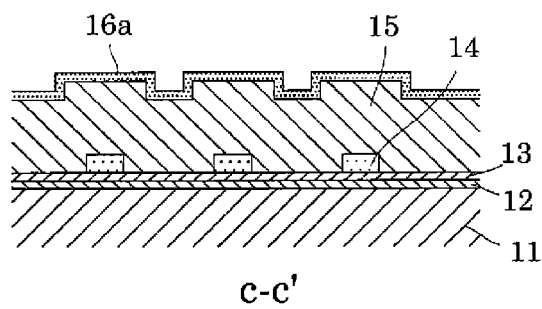
Figure 17A:
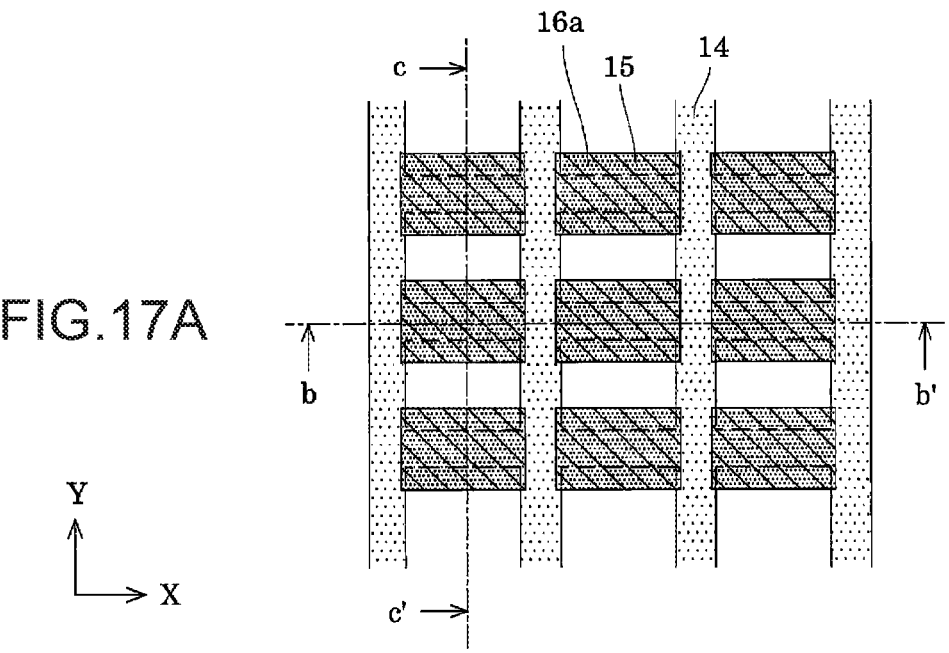
FIGS. 17A, 17B and 17C show a plan view and a cross-sectional view illustrating a manufacturing example of the ultrasound sensor according to Embodiment 2.
Figure 17B:
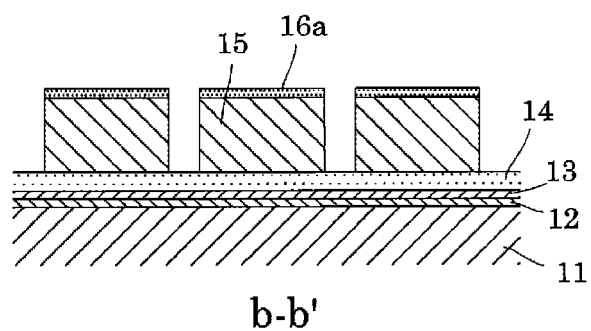
Figure 17C:
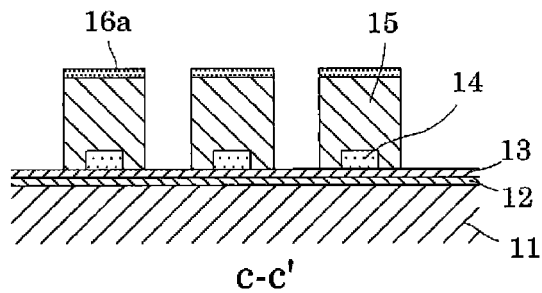

Next, as illustrated in FIGS. 16A, 16B, and 16C, the primary second electrode 16a is formed by a sputtering method, a thermal oxidation method or the like on the piezoelectric layer 15 and, as illustrated in FIGS. 17A, 17B and 17C, the primary second electrode 16a and the piezoelectric layer 15 are subjected to patterning for each piezoelectric element.

Figure 18A:
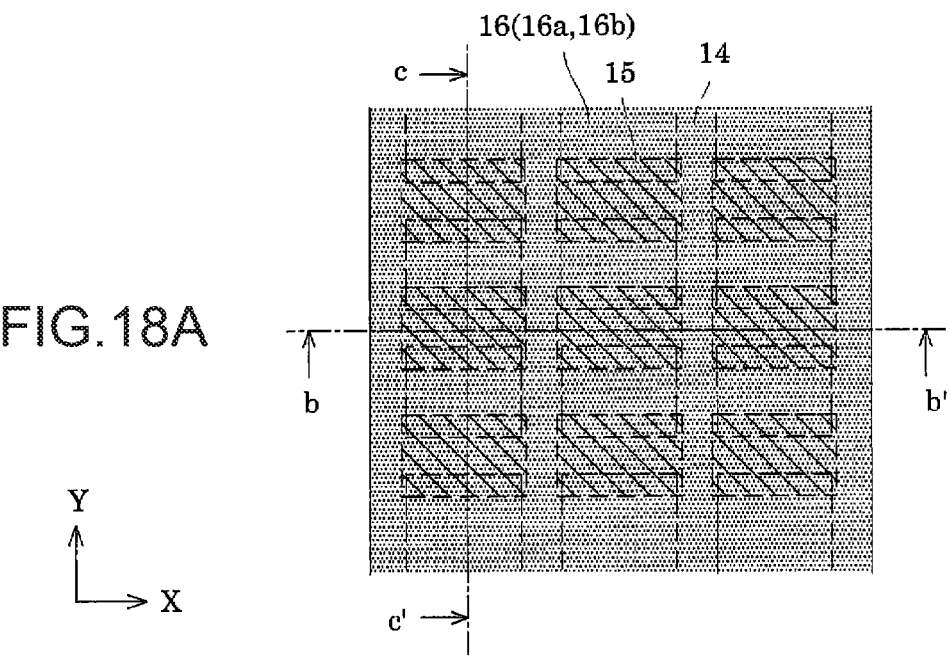
FIGS. 18A, 18B and 18C show a plan view and a cross-sectional view illustrating a manufacturing example of the ultrasound sensor according to Embodiment 2.
Figure 18B:
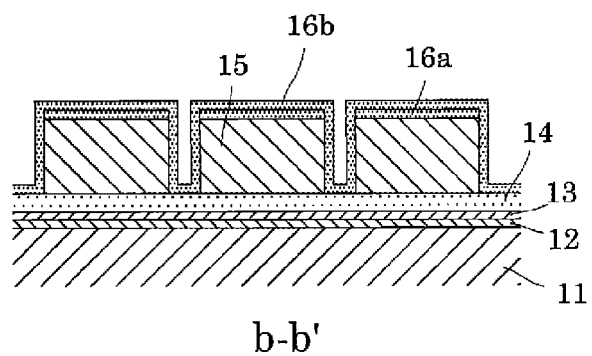
Figure 18C:
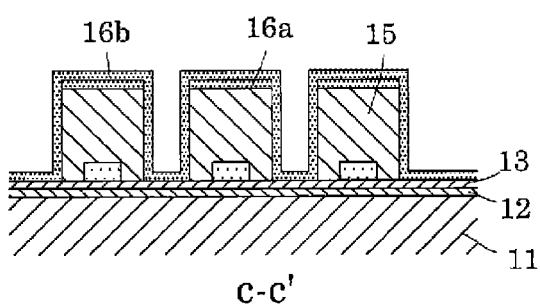
Figure 19A:
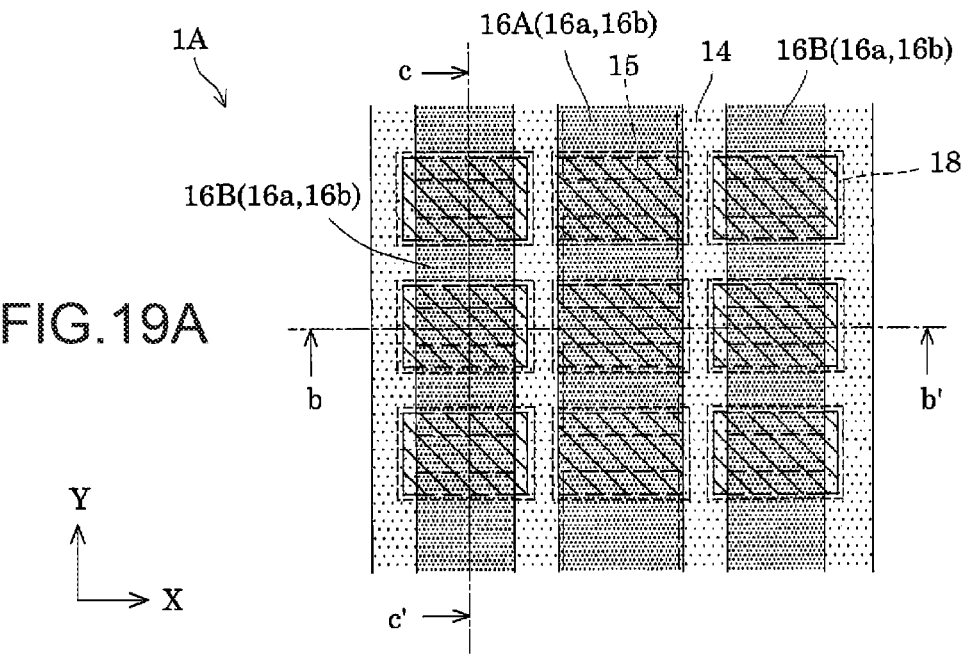
FIGS. 19A, 19B and 19C show a plan view and a cross-sectional view illustrating a manufacturing example of the ultrasound sensor according to Embodiment 2.
Figure 19B:
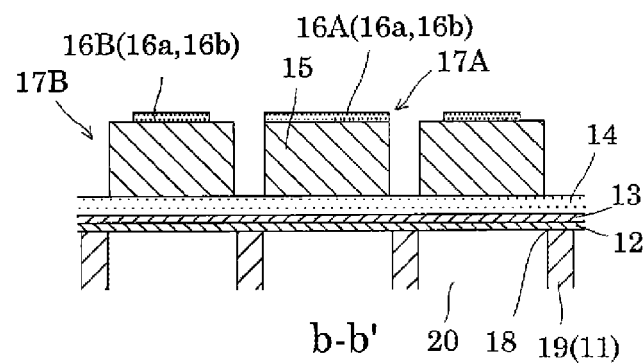
Figure 19C:
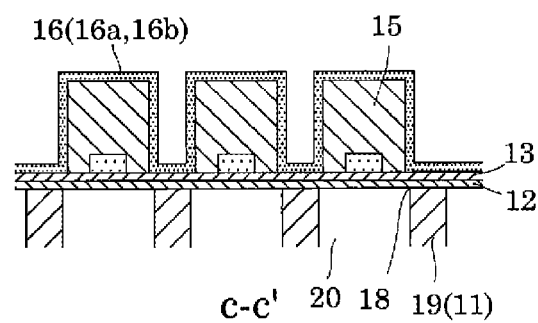

Next, as illustrated in FIGS. 18A, 18B and 18C, the secondary second electrode 16b is provided in the same manner of the primary second electrode 16a. As illustrated in FIGS. 19A, 19B and 19C, the primary second electrode 16a and the secondary second electrode 16b are subjected to patterning and divided for each row in the second direction Y such that they are continuously arranged for each row in the first direction X. In the center raw of the drawing, the second electrode 16A is wider, of which width is the approximately same as that of the piezoelectric layer 15. In the rows on both sides, the narrower second electrodes 16B are provided. With this configuration, the dedicated transmission piezoelectric element 17A having the wider second electrode 16A and the dedicated reception piezoelectric element 17B having the narrower second electrode 16B are formed.

Subsequently, a protective film is formed and subjected to patterning as appropriate, and then the opening portion 18 is formed. Thereby, the ultrasound sensor 1A is obtained.

This method also enables that the dedicated transmission piezoelectric element 17A and the dedicated reception piezoelectric element 17B can be manufactured and transmission performance and reception performance can be improved, respectively, only by varying the patterning of the secondary second electrode 16b, which is performed in a last stage of the film-forming process of the ultrasound sensor.

Embodiment 3

Figure 20A:
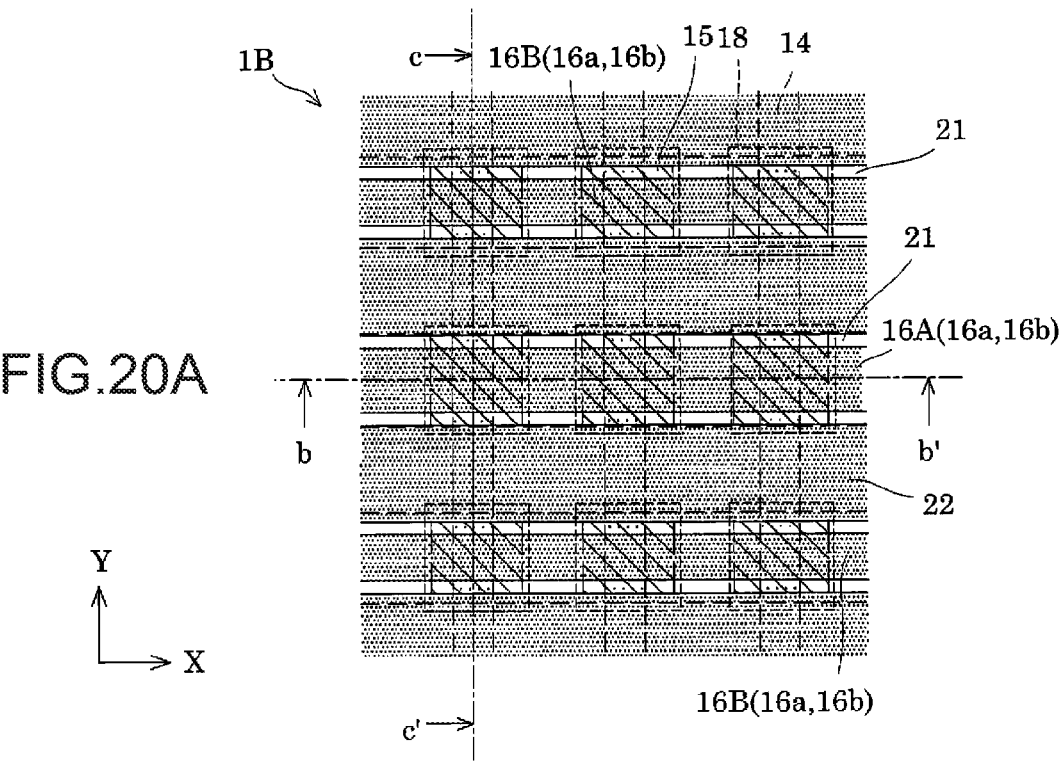
FIGS. 20A, 20B and 20C show a plan view and a cross-sectional view of the ultrasound sensor according to Embodiment 3.
Figure 20B:
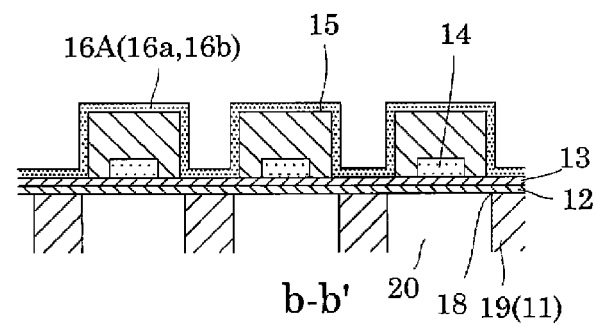
Figure 20C:
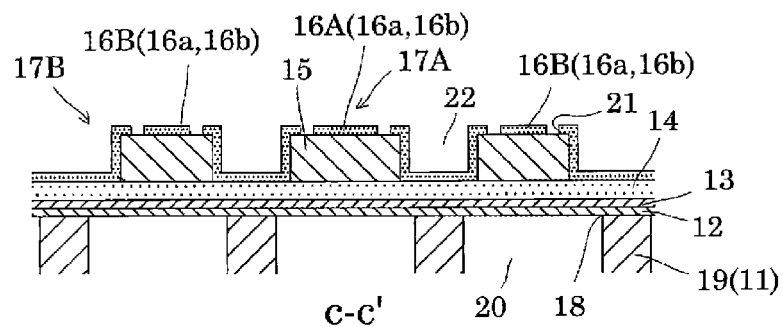

FIGS. 20A, 20B and 20C show an ultrasound sensor 1B of Embodiment 3. In the present embodiment, when patterning the secondary second electrode 16b, the second electrode 16 and a discontinuous electrode 22 which is electrically discontinued from the second electrode 16 are separated by a groove 21 instead of removing unnecessary portion of the second electrode 16. By varying a forming position of the groove 21, the wider second electrode 16A is provided in a center row in the vertical direction, the narrower second electrodes 16B are provided on both sides in the vertical direction, the dedicated transmission piezoelectric element 17A is provided in a center row and the dedicated reception piezoelectric elements 17B are provided on both sides in the vertical direction.

This process also enables that the dedicated transmission piezoelectric element 17A and the dedicated reception piezoelectric element 17B can be manufactured and transmission performance and reception performance can be improved, respectively, only by varying the patterning of the secondary second electrode 16b, which is performed in a last stage of the film-forming process of the ultrasound sensor.

Embodiment 4

Figure 21A:
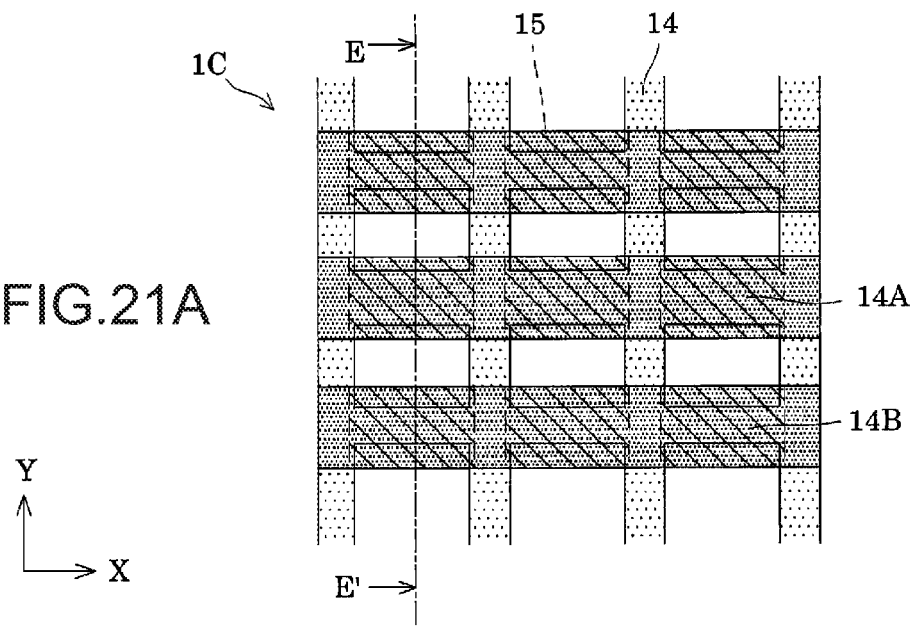
FIGS. 21A and 21B show a plan view and a cross-sectional view of the ultrasound sensor according to Embodiment 4.
Figure 21B:
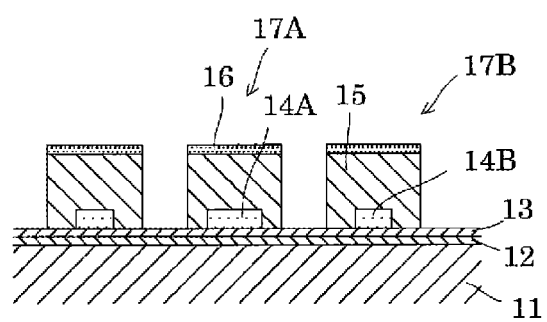

FIGS. 21A and 21B show an ultrasound sensor 1C of Embodiment 4. In the present embodiment, the width of the first electrodes 14 is varied so as to serve as the dedicated transmission element and the dedicated reception element instead of varying the width of the second electrode 16. In the present embodiment, when patterning the first electrode 14, i.e. the common electrode, a center row in the vertical direction is subjected to patterning so as to be a wider first electrode 14A, and rows on both sides in the vertical direction are subjected to patterning so as to be a narrower first electrodes 14B. After that, the same processes as those of the embodiments stated above are employed. The dedicated transmission piezoelectric element 17A having the wider first electrode 14A is provided in the center row in the vertical direction, and the dedicated reception piezoelectric elements 17B having the narrower first electrodes 14B are provided in the rows on both sides in the vertical direction.

This process also enables that the dedicated transmission piezoelectric element 17A and the dedicated reception piezoelectric element 17B can be manufactured and transmission performance and reception performance can be improved, respectively, only by varying the patterning of the first electrode 14, which is performed in a first stage of the film-forming process of the ultrasound sensor.

Other Embodiments

Although not described in each of the above-described embodiments, it is possible to use a configuration in which the opposite side to the piezoelectric element 17 of the diaphragm becomes a pass-through region for ultrasonic waves transmitted towards a measurement target or ultrasound waves reflected from the measurement target (echo signal). Accordingly, it is possible to simplify the configuration of the opposite side to the piezoelectric element 17 of the diaphragm, and possible to ensure a favorable pass-through region for ultrasonic waves and the like. An electrical region of the electrodes, wirings and the like and the contact and fixing region of each member is distanced from the measurement target, and it becomes easier to prevent contamination or leakage current between these and the measurement target. Accordingly, it is possible to also favorably apply the invention a medical device which is particularly averse to contamination or leakage current, for example, ultrasound diagnostic equipment, blood pressure gages, and eye pressure gages.

In general, the opening portion 18 of the substrate 11 is filled with a resin serving as the acoustic matching layer, such as silicone oil, a silicone resin or a silicone rubber, and the opening portion 18 is sealed with a lens member through which the ultrasound can be passed. Thereby, the acoustic impedance difference between the piezoelectric element 17 and the measurement target can be reduced, and the ultrasound can be transmitted efficiently to the measurement target side.

Furthermore, although not described in the above-described embodiments, it is preferable that a sealing plate that seals the region which includes the piezoelectric element 17 is bonded to the substrate 11. Thereby, because it is possible to physically protect the piezoelectric element 17, and the strength of the ultrasound sensor 1 also increases, it is possible to increase the structural stability. It is possible for the handling properties of the ultrasound sensor 1 which includes the piezoelectric elements 17 to be improved in a case where the piezoelectric elements 17 are formed as thin films.

In the above-described embodiment, although an example is given in which the opening portion 18 is formed for each piezoelectric element 17, there is no limitation thereto, and the openings may be formed corresponding to a plurality of piezoelectric elements 17. For example, an opening which is shared by a row of piezoelectric elements 17 arranged along the scanning direction may be provided or one opening may be formed for all piezoelectric elements 17. Although the vibration states of the piezoelectric elements 17 become different in a case where an opening shared for a plurality of piezoelectric elements 17 is provided, a pressing member or the like is provided between each of the piezoelectric elements 17 from the opposite side to the substrate 11 of the diaphragm, and similar vibration may be performed as a case where independent openings are provided.

Figure 22:
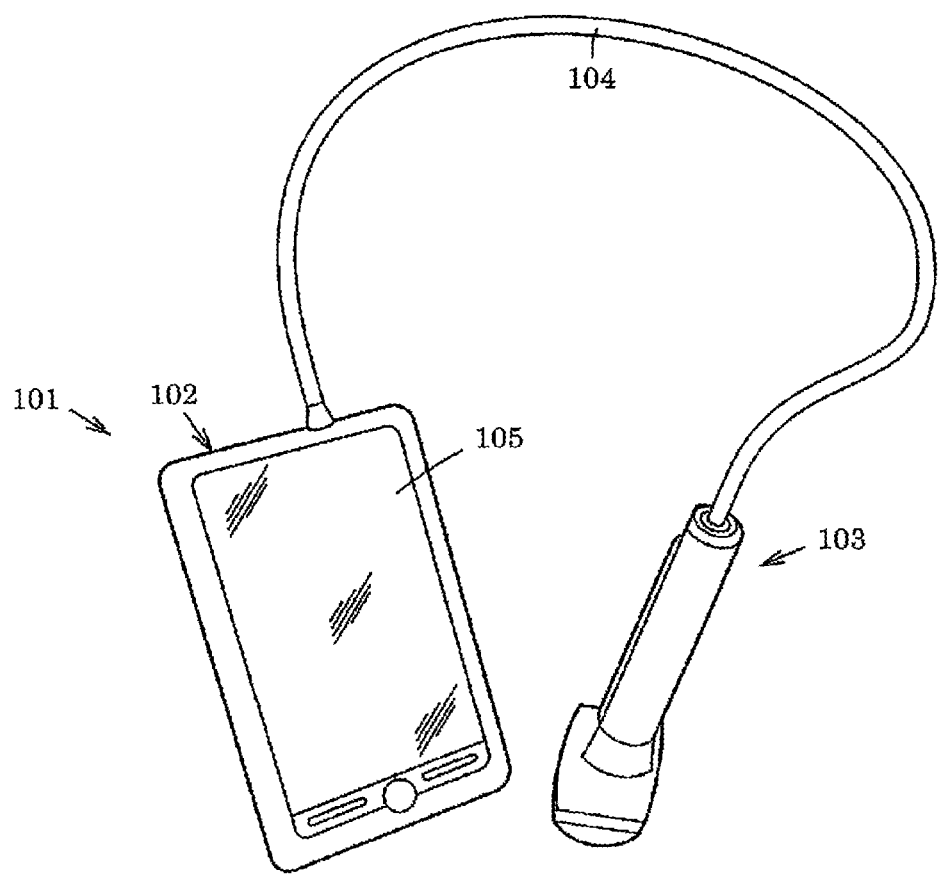
FIG. 22 is a perspective view illustrating an example of an ultrasonic diagnostic apparatus.
Figure 23:
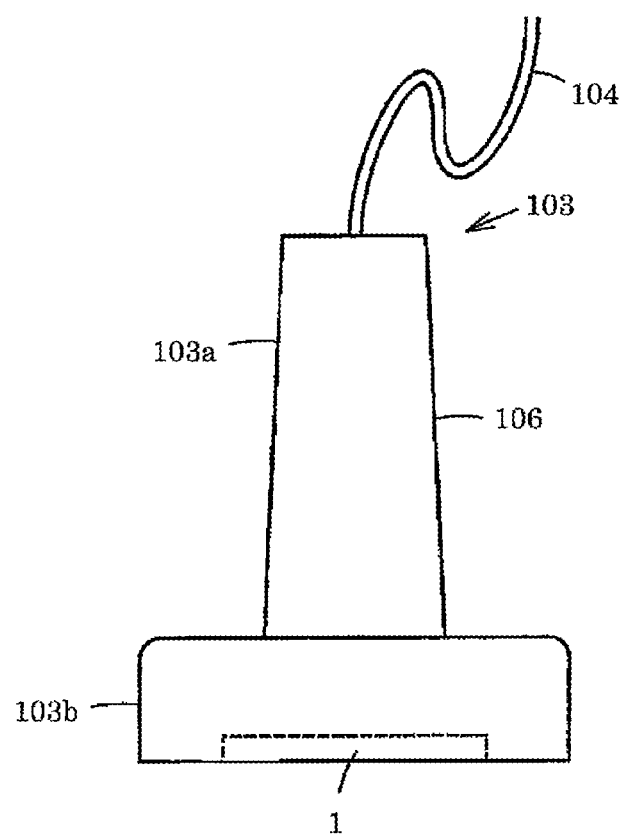
FIG. 23 is a perspective view illustrating an example of an ultrasound probe.

Here, an example of an ultrasonic diagnostic apparatus using the ultrasound sensor described above will be described. FIG. 22 is a perspective view illustrating a schematic configuration of an example of the ultrasonic diagnostic apparatus, and FIG. 23 is a cross-sectional view illustrating the ultrasound probe.

As illustrated in the drawings, an ultrasonic diagnostic apparatus 101 is provided with a device terminal 102 and an ultrasound probe (probe) 103. The device terminal 102 and the ultrasound probe 103 are connected by a cable 104. The device terminal 102 and the ultrasound probe 103 exchange electrical signals through the cable 104. A display panel (display device) 105 is incorporated in the device terminal 102. A screen of the display panel 105 is exposed in the surface of the device terminal 102. In the device terminal 102, an image is generated based on ultrasonic waves transmitted from the ultrasound sensor 1 of the ultrasound probe 103 and detected. The imaged detection results are displayed on the screen of the display panel 105.

The ultrasound probe 103 includes a housing 106. The ultrasound sensor 1 in which a plurality of ultrasound sensor elements 10 are two-dimensionally arranged in the first direction X and the second direction Y is stored in the housing 106. The ultrasound sensor 1 is provided so that the surface thereof is exposed in the surface of the housing 106. The ultrasound sensor 1 outputs ultrasonic waves from the surface and receives the reflected waves of the ultrasound. It is possible to provide the ultrasound probe 103 with a probe head 103b which is freely detachable from a probe main body 103a. At this time, it is possible for the ultrasound sensor 1 to be incorporated in the housing 106 of the probe head 103b. The ultrasound sensor 1 is formed with the ultrasound sensor elements 10 arranged two-dimensionally in the first direction X and the second direction Y.

The invention claimed is:

1. An ultrasound sensor comprising:
a substrate which has a plurality of openings;
a diaphragm which is provided on the substrate so as to cover the plurality of openings;
a plurality of first electrodes which is provided at a first side of the diaphragm opposite to the plurality of openings, the plurality of first electrodes being arranged along an X-direction, each of the plurality of first electrodes linearly extending along a Y-direction orthogonal to the X-direction;
a plurality of second electrodes which is provided at the first side of the diaphragm, the plurality of second electrodes being arranged along the Y-direction, each of the plurality of second electrodes linearly extending along the X-direction; and
a plurality of piezoelectric layers which is provided between the plurality of first electrodes and the plurality of second electrodes at positions in which the plurality of first electrodes and the plurality of second electrodes overlap with each other in a plan view,
wherein, in a Z-direction orthogonal to the X-direction and the Y-direction, each area in which the plurality of first electrodes, the plurality of piezoelectric layers, and the plurality of second electrodes are overlapped is an active area,
a width of one electrode of the plurality of first electrodes or one electrode of the plurality of second electrodes is larger than a remainder of the first and second electrodes so that the active areas have different sizes from each other,
wherein the plurality of openings have substantially equal sizes in the plan view,
the plurality of piezoelectric layers corresponding to the plurality of openings have equal sizes in the plan view, and
a size of the one electrode of the plurality of first electrodes corresponding to one of the openings and a size of the one electrode of the plurality of second electrodes corresponding to one of the plurality of openings are different from each other in the plan view.

2. The ultrasound sensor according to claim 1,
wherein the diaphragm includes movable areas that are configured to move by driving the active areas, each movable area corresponding to one of the active areas, and each of the active areas is provided within each of the movable areas, and
the movable areas have equal sizes in the plan view.

3. The ultrasound sensor according to claim 1,
wherein a width in the Y-direction of the one electrode of the plurality of second electrodes is larger than a width in the Y-direction of another electrode of the plurality of second electrodes.

4. The ultrasound sensor according to claim 1,
wherein a width in the Y-direction of the one electrode of the plurality of second electrodes is the same as a width in the Y-direction of a corresponding piezoelectric layer of the plurality of piezoelectric layers, and
a width in the Y-direction of another electrode of the plurality of second electrodes is smaller than a width in the Y-direction of another corresponding piezoelectric layer of the plurality of piezoelectric layers.

5. The ultrasound sensor according to claim 1,
wherein the plurality of piezoelectric layers is formed of substantially the same piezoelectric material.

6. An ultrasound sensor comprising:
a substrate which has a plurality of openings;
a diaphragm which is provided on the substrate so as to cover the plurality of openings;
a plurality of first electrodes which is provided at a first side of the diaphragm opposite to the plurality of openings, the plurality of first electrodes being arranged along an X-direction, each of the plurality of first electrodes linearly extending along a Y-direction orthogonal to the X-direction;
a plurality of second electrodes which is provided at the first side of the diaphragm, the plurality of second electrodes being arranged along the Y-direction, each of the plurality of second electrodes linearly extending along the X-direction; and
a plurality of piezoelectric layers which is provided between the plurality of first electrodes and the plurality of second electrodes at positions in which the plurality of first electrodes and the plurality of second electrodes overlap with each other in a plan view,
wherein, in a Z-direction orthogonal to the X-direction and the Y-direction, each area in which the plurality of first electrodes, the plurality of piezoelectric layers, and the plurality of second electrodes are overlapped is an active area,
a width of one electrode of the plurality of first electrodes or one electrode of the plurality of second electrodes is larger than a remainder of the first and second electrodes so that the active areas have different sizes from each other,
wherein a width in the Y-direction of the one electrode of the plurality of second electrodes is the same as a width in the Y-direction of a corresponding piezoelectric layer of the plurality of piezoelectric layers, and
a width in the Y-direction of another electrode of the plurality of second electrodes is smaller than a width in the Y-direction of another corresponding piezoelectric layer of the plurality of piezoelectric layers.

* * * * *